US012788636B2

(12) United States Patent
DiGrazia

(10) Patent No.: US 12,788,636 B2
(45) **Date of Patent: *Nov. 10, 2026**

(54) APPENDAGE AND LIMB PROTECTIVE WRAPPING

(71) Applicant: Jennifer DiGrazia, Parrish, FL (US)

(72) Inventor: Jennifer DiGrazia, Parrish, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/344,080

(22) Filed: Sep. 29, 2025

(65) Prior Publication Data

US 2026/0026973 A1 Jan. 29, 2026

Related U.S. Application Data

(63) Continuation of application No. 16/576,128, filed on Sep. 19, 2019, now Pat. No. 12,427,067, which is a continuation of application No. 13/732,355, filed on Dec. 31, 2012, now Pat. No. 10,517,765, which is a continuation-in-part of application No. 13/807,404, filed as application No. PCT/US2011/042216 on Jun. 28, 2011, now Pat. No. 9,833,361, which is a (Continued)

(51) Int. Cl.
*A61F 5/00* (2006.01)
*A61F 13/00* (2006.01)
*A61F 13/02* (2006.01)

(52) U.S. Cl.
CPC .... *A61F 13/00051* (2013.01); *A61F 13/0273* (2013.01)

(58) Field of Classification Search
USPC .............................................................. 602/3
See application file for complete search history.

(56) References Cited

U.S. PATENT DOCUMENTS

| | | | |
|---|---|---|---|
| 250,154 | A | 11/1881 | Master |
| 1,457,858 | A | 6/1923 | William |

(Continued)

FOREIGN PATENT DOCUMENTS

| | | | |
|---|---|---|---|
| WO | 9802120 A1 | 1/1998 | |
| WO | 0238096 A2 | 5/2002 | |
| WO | 02053075 A1 | 7/2002 | |

OTHER PUBLICATIONS

JP 4355632 B2 Translation (Year: 2009).*

(Continued)

*Primary Examiner* — Kim M Lewis
(74) *Attorney, Agent, or Firm* — Shore IP Group, PLLC; Sean R. Wilsusen

(57) ABSTRACT

Wound/bandage protectors configured as a wrap, a sock/mitten, which may be made out of stretchable material. The wrap may have one or more fastening straps as well as possibly a first catch fastening surface. The sock/mitten may have a fastening strap and a sheath. The wrap, the sock/mitten, and the bandages may have apertures and aperture covers. The wrap may have one or more fastening straps as well as possibly a first catch fastening surface and an accessory holder. The sock/mitten may have a fastening strap and a sheath. The strap may be attached to an internal side of a body of the sock/mitten and extend out a slit. The internal portion of the strap having a non-slip grip surface and the external portion of the strip configured to fasten to the body or to the strap itself.

16 Claims, 22 Drawing Sheets

Related U.S. Application Data continuation-in-part of application No. 13/004,866, filed on Jan. 11, 2011, now abandoned, and a continuation-in-part of application No. 12/826,644, filed on Jun. 29, 2010, now Pat. No. 8,591,447, said application No. 13/004,866 is a continuation-in-part of application No. 12/826,644, filed on Jun. 29, 2010, now Pat. No. 8,591,447.

(60) Provisional application No. 61/453,341, filed on Mar. 16, 2011, provisional application No. 61/360,873, filed on Jul. 1, 2010.

(56) References Cited

U.S. PATENT DOCUMENTS

| | | | | |
|---|---|---|---|---|
| 2,233,209 | A | 2/1941 | Herzog | |
| 2,310,082 | A | 2/1943 | Holbrooke | |
| 2,321,363 | A | 6/1943 | Crowley | |
| 3,245,406 | A | 4/1966 | Chardack | |
| 3,329,143 | A | 7/1967 | Gordon | |
| 3,442,270 | A | 5/1969 | Charles | |
| 3,504,672 | A | 4/1970 | Moon | |
| 3,561,436 | A | 2/1971 | Gaylord, Jr. | |
| 3,657,741 | A | 4/1972 | Blanco | |
| 3,741,203 | A * | 6/1973 | Liman | A61F 15/004 602/3 |
| 3,874,014 | A | 4/1975 | Davey | |
| 3,880,161 | A | 4/1975 | Fossel | |
| 3,970,079 | A | 7/1976 | Gaylord, Jr. | |
| 4,036,220 | A | 7/1977 | Bellasalma | |
| 4,088,136 | A | 5/1978 | Hasslinger et al. | |
| 4,126,130 | A | 11/1978 | Cowden et al. | |
| 4,254,765 | A | 3/1981 | Brown et al. | |
| 4,355,635 | A | 10/1982 | Bihl et al. | |
| 4,461,098 | A | 7/1984 | Diegelman | |
| 4,530,350 | A | 7/1985 | Brown et al. | |
| 4,665,909 | A | 5/1987 | Trainor | |
| 4,671,787 | A | 6/1987 | Widman | |
| 4,724,831 | A | 2/1988 | Huntjens | |
| 4,881,276 | A | 11/1989 | Swan | |
| 4,977,893 | A | 12/1990 | Hunt | |
| 4,991,234 | A | 2/1991 | Greenberg | |
| 5,085,210 | A | 2/1992 | Smith, III | |
| 5,137,508 | A | 8/1992 | Engman | |
| D340,985 | S | 11/1993 | Arginsky | |
| 5,271,745 | A | 12/1993 | Fentress et al. | |
| 5,395,302 | A * | 3/1995 | Botha | A61F 15/004 128/849 |
| 5,439,438 | A * | 8/1995 | Ersfeld | A61F 13/041 602/3 |
| 5,513,658 | A | 5/1996 | Goseki | |
| 5,538,500 | A | 7/1996 | Peterson | |
| 5,591,122 | A | 1/1997 | Yewer, Jr. | |
| D389,244 | S | 1/1998 | Dunshee et al. | |
| 5,720,713 | A | 2/1998 | Hutchison | |
| 5,735,807 | A * | 4/1998 | Cropper | A61F 5/0109 602/26 |
| 5,755,698 | A | 5/1998 | Kagan et al. | |
| 5,786,365 | A | 7/1998 | Heitsch et al. | |
| 5,817,038 | A | 10/1998 | Orange et al. | |
| 5,843,018 | A | 12/1998 | Shesol et al. | |
| 5,865,776 | A | 2/1999 | Springs | |
| 5,873,365 | A | 2/1999 | Brown | |
| 5,876,365 | A | 3/1999 | Hart | |
| 5,897,519 | A | 4/1999 | Shesol et al. | |
| 5,921,949 | A | 7/1999 | Dray | |
| 6,032,289 | A | 3/2000 | Villapiano | |
| 6,059,834 | A | 5/2000 | Springs | |
| 6,164,279 | A | 12/2000 | Tweedle | |
| 6,258,051 | B1 | 7/2001 | Shesol et al. | |
| 6,307,118 | B1 | 10/2001 | Reich | |
| 6,399,852 | B1 | 6/2002 | Barron | |
| 6,659,970 | B1 | 12/2003 | Woodworth et al. | |
| 6,664,434 | B2 | 12/2003 | Cominsky | |
| 6,681,404 | B1 | 1/2004 | Adlard et al. | |
| 6,762,337 | B2 | 7/2004 | Boukanov et al. | |
| 6,892,733 | B2 | 5/2005 | Clinton | |
| 6,932,785 | B1 | 8/2005 | Shesol | |
| 7,004,922 | B1 | 2/2006 | Shesol | |
| 7,025,738 | B2 | 4/2006 | Hall | |
| 7,160,262 | B2 | 1/2007 | Wicks | |
| D573,260 | S | 7/2008 | Dunshee | |
| 8,529,481 | B1 | 9/2013 | Lois | |
| 9,833,361 | B2 | 12/2017 | DiGrazia | |
| 12,427,067 | B2 * | 9/2025 | DiGrazia | A61F 13/00051 |
| 12,427,068 | B2 * | 9/2025 | DiGrazia | A61F 13/0203 |
| 2003/0139696 | A1 | 7/2003 | Boukanov et al. | |
| 2003/0149389 | A1 | 8/2003 | Daneshvar | |
| 2004/0260224 | A1 | 12/2004 | Binder et al. | |
| 2004/0267179 | A1 | 12/2004 | Lerman | |
| 2005/0192524 | A1 | 9/2005 | Lipshaw et al. | |
| 2005/0261617 | A1 | 11/2005 | Hall | |
| 2006/0116621 | A1 | 6/2006 | Barker | |
| 2006/0116622 | A1 | 6/2006 | Pike | |
| 2007/0232974 | A1 | 10/2007 | Serola | |
| 2009/0221945 | A1 | 9/2009 | Andersson et al. | |
| 2010/0100024 | A1 | 4/2010 | Reid, Jr. | |
| 2010/0331747 | A1 | 12/2010 | Ferenc | |
| 2011/0137223 | A1 | 6/2011 | Daniel | |
| 2011/0277283 | A1 | 11/2011 | Ward, IV | |
| 2012/0203152 | A1 | 8/2012 | Thompson | |
| 2013/0123679 | A1 | 5/2013 | DiGrazia | |

OTHER PUBLICATIONS

Ex Parte Quayle Action dated May 5, 2016 in corresponding U.S. Appl. No. 13,732,355.
Final Office Action dated Apr. 30, 2015 in corresponding U.S. Appl. No. 13,732,355.
Final Office Action dated May 18, 2017 in corresponding U.S. Appl. No. 13,732,355.
International Preliminary Report on Patentability Dated Jul. 9, 2015 For Application Serial No. PCT/US2013/078532.
Notice of Allowance dated May 8, 2019 in corresponding U.S. Appl. No. 13,732,355.
Office Action dated Sep. 24, 2014 in corresponding U.S. Appl. No. 13,732,355.
Office Action dated Sep. 24, 2018 in corresponding U.S. Appl. No. 13,732,355.
Office Action Dated Sep. 30, 2022 In Related U.S. Appl. No. 17/060,912.
Office Action dated Oct. 26, 2016 in corresponding U.S. Appl. No. 13,732,355.
Office Action Dated Oct. 29, 2020 In Corresponding U.S. Appl. No. 15/831,692.
Office Action Dated Apr. 26, 2023 In Corresponding U.S. Appl. No. 15/831,692.
Office Action Dated May 10, 2023 In Corresponding U.S. Appl. No. 17/060,950.
Office Action Dated Aug. 12, 2016 For U.S. Appl. No. 13/807,404.
Office Action Dated Dec. 23, 2015 For U.S. Appl. No. 13/807,404.
US FOA dated Aug. 14, 2014 for U.S. Appl. No. 13/807,404.
US OA dated Dec. 3, 2014 for U.S. Appl. No. 13/807,404.
Von Moody, "Polyvinyl Chloride Pastisol Coating", 2004 (p. 2 of 14).
Non-Final Office Action mailed Feb. 13, 2026 in related U.S. Appl. No. 19/344,032.

* cited by examiner

FIG. 19A
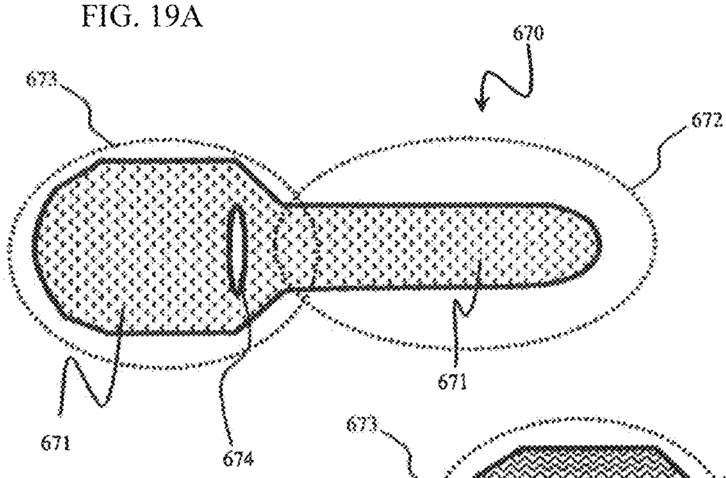
FIG. 19B
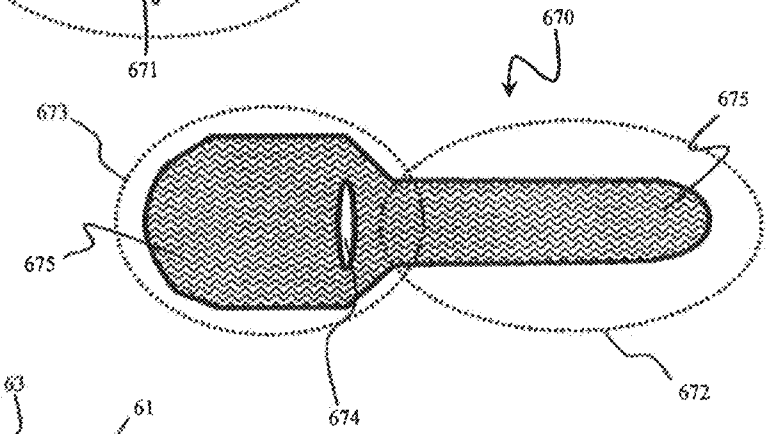
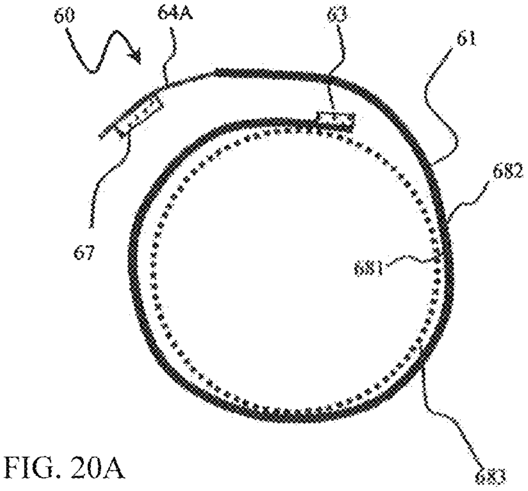
FIG. 20A
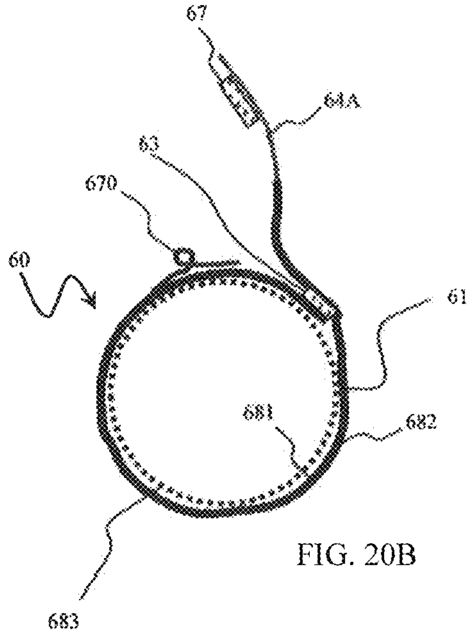
FIG. 20B
FIG. 20C
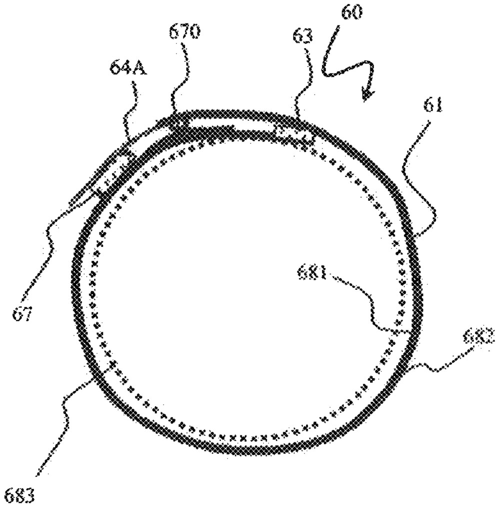

FIG. 21
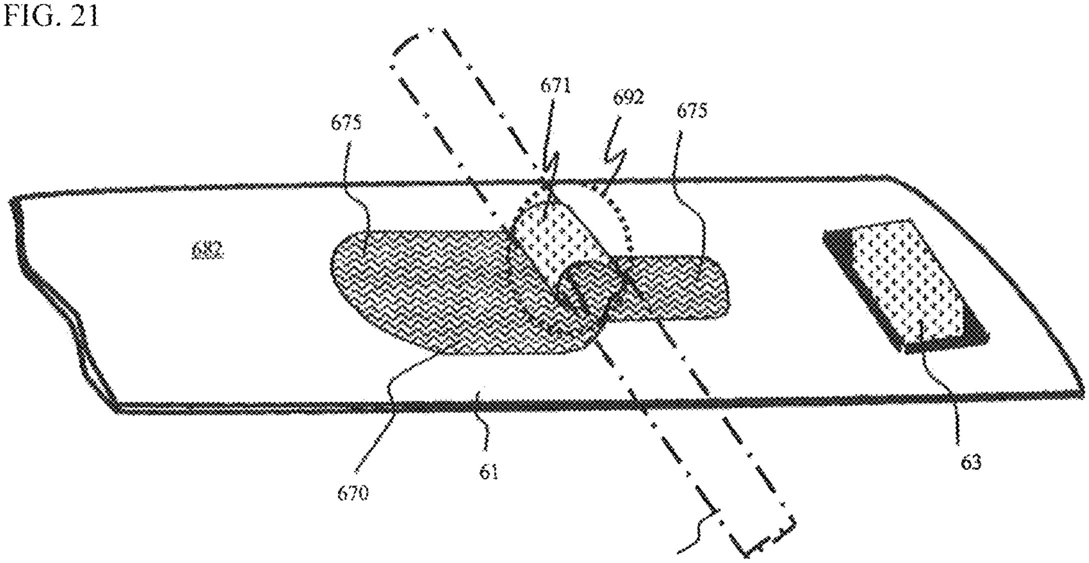
FIG. 22A
FIG. 22B
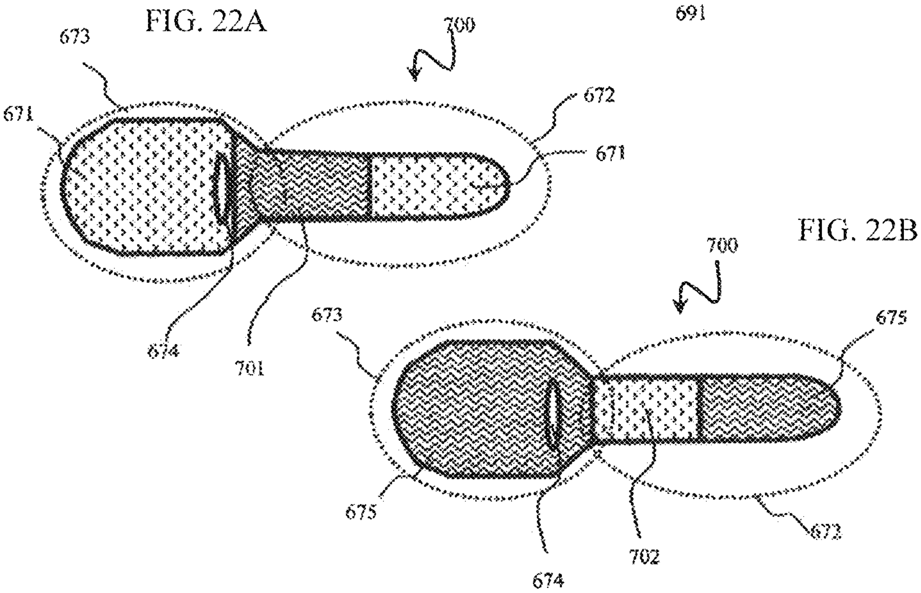
FIG. 23
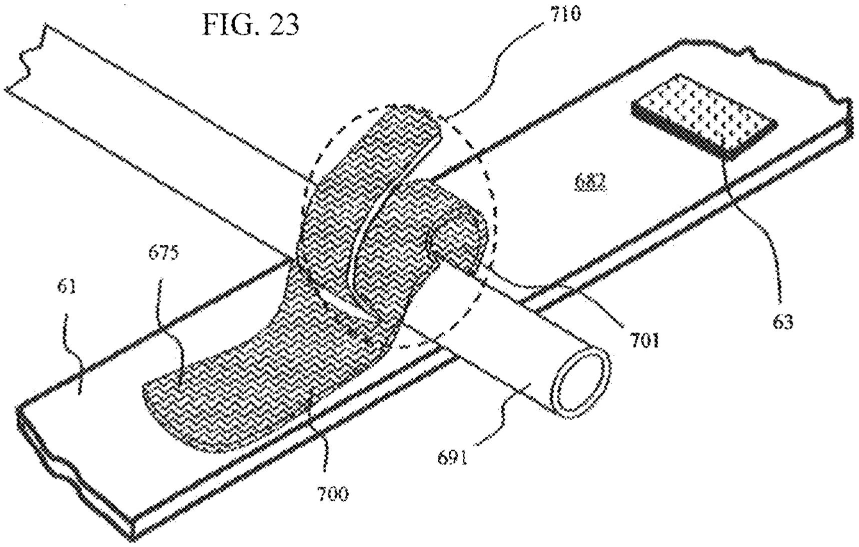

FIG. 24A
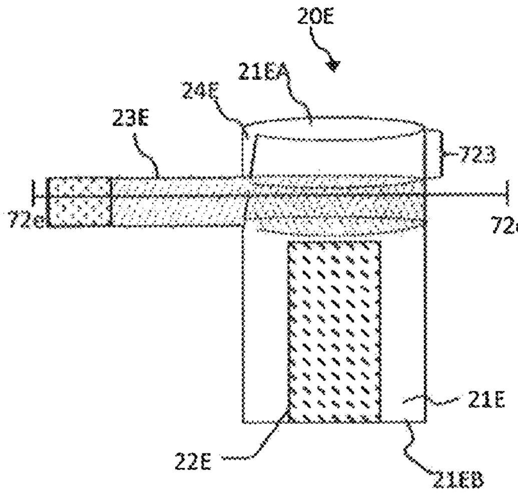
FIG. 24B
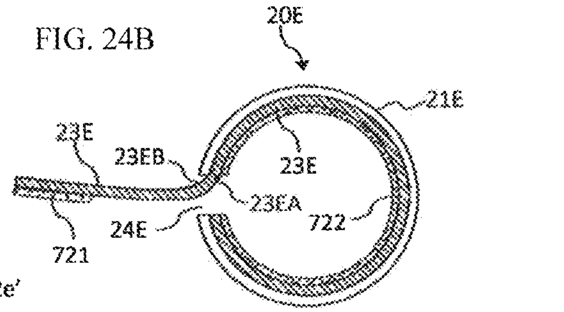
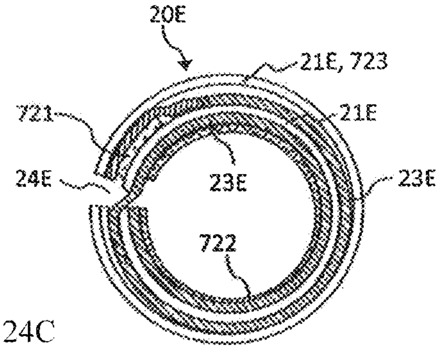
FIG. 24C
FIG. 25A
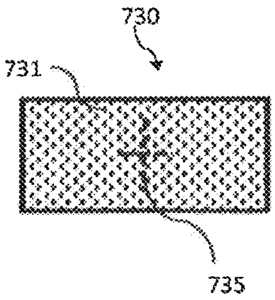
FIG. 25B
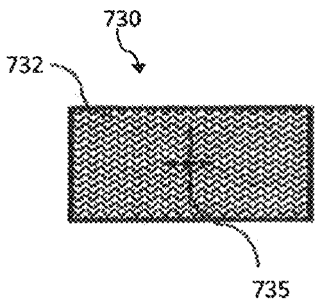
FIG. 25C
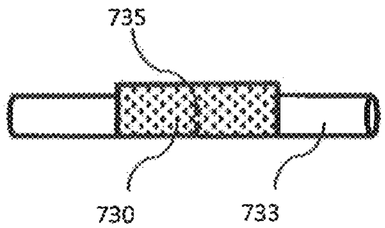
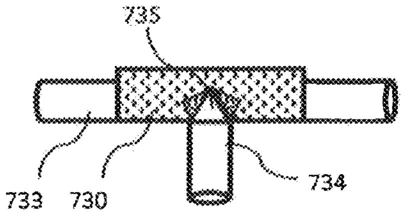
FIG. 25D

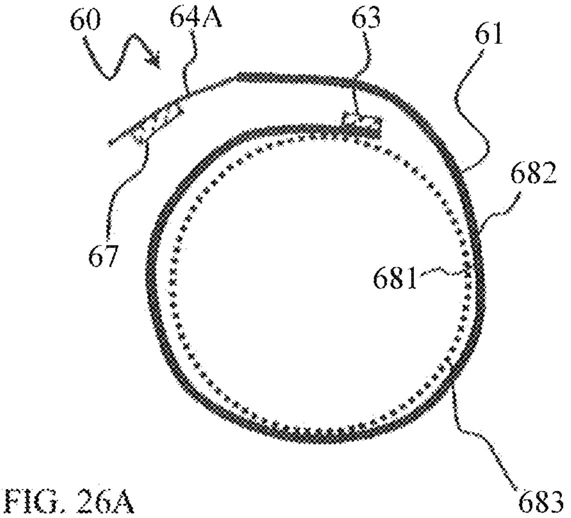
FIG. 26A
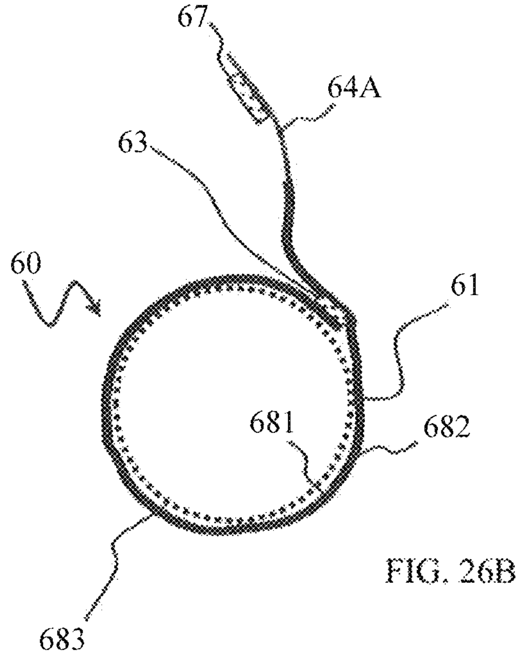
FIG. 26B
FIG. 26C
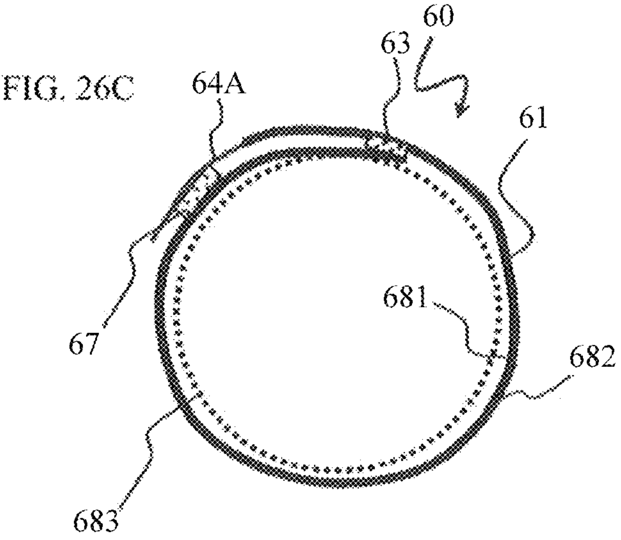

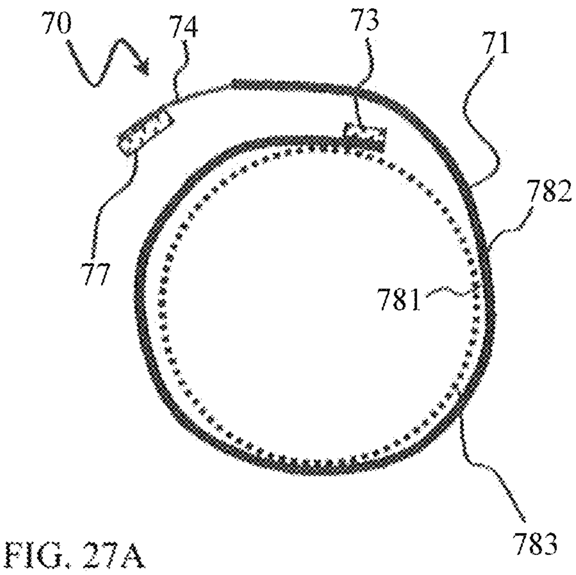
FIG. 27A
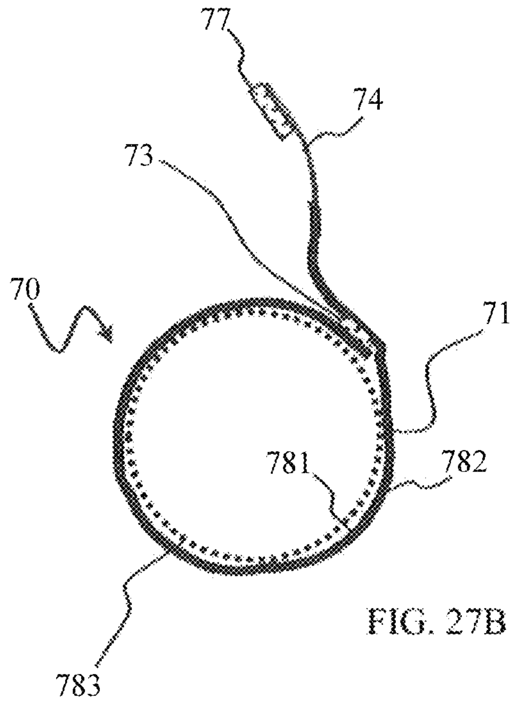
FIG. 27B
FIG. 27C
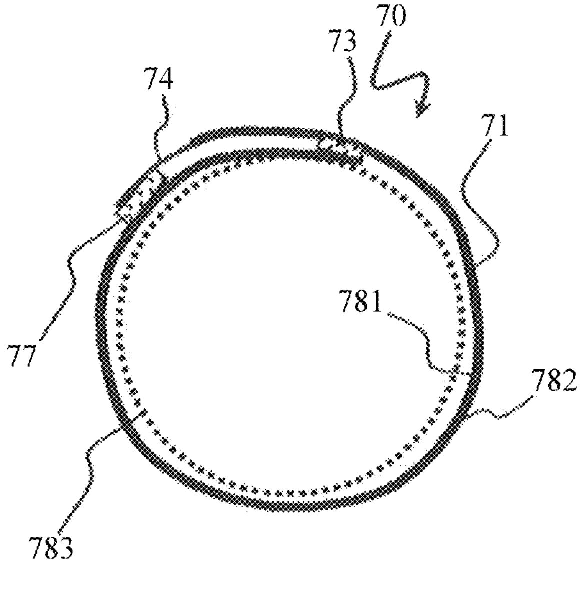

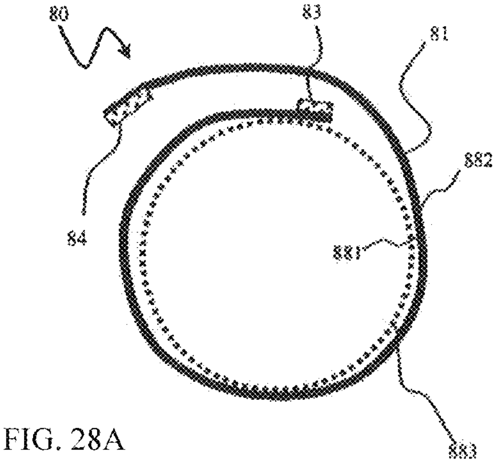
FIG. 28A
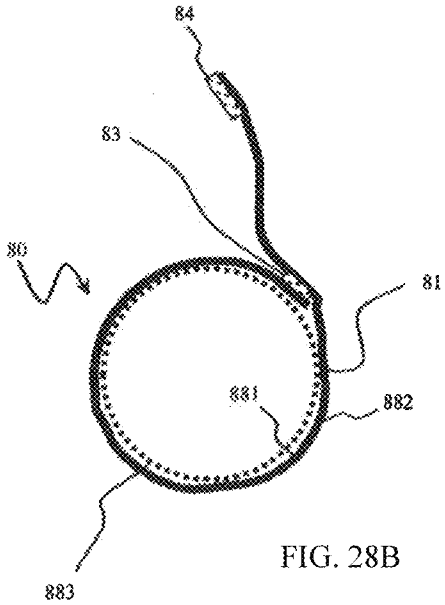
FIG. 28B
FIG. 28C
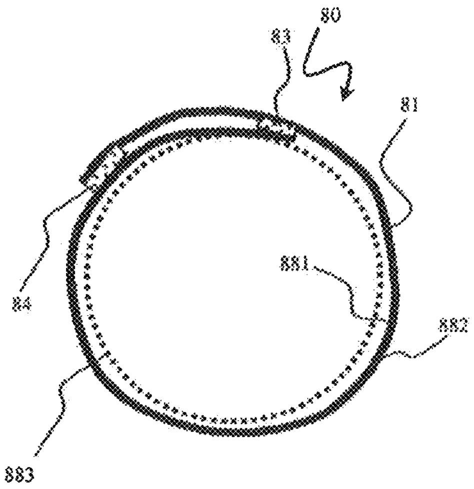

APPENDAGE AND LIMB PROTECTIVE WRAPPING

CROSS-REFERENCE TO RELATED APPLICATIONS

This application is a continuation of U.S. patent application Ser. No. 16,576,128 filed on Sep. 19, 2019, which is a continuation of U.S. patent application Ser. No. 13/732,355 filed on Dec. 31, 2012, now U.S. Pat. No. 10,517,765 issued on Dec. 31, 2019, which is a continuation-in-part of U.S. patent application Ser. No. 13/807,404 filed on Dec. 28, 2012, now U.S. Pat. No. 9,833,361 issued on Dec. 5, 2017, which is a continuation-in-part of U.S. patent application Ser. No. 12/826,644 filed on Jun. 29, 2010, now U.S. Pat. No. 8,591,447 issued on Nov. 26, 2013, and is a continuation-in-part of U.S. patent application Ser. No. 13/004,866 filed on Jan. 11, 2011.

U.S. patent application Ser. No. 13/807,404 is the national phase entry of International Application No. PCT/US2011/042216 filed on Jun. 28, 2011. International Application No. PCT/US2011/042216 is a continuation-in-part of U.S. patent application Ser. No. 12/826,644, and is a continuation-in-part of U.S. patent application Ser. No. 13/004,866 and claims the benefit of U.S. Provisional Patent Application No. 61/360,873 filed on Jul. 1, 2010 and U.S. Provisional Patent Application No. 61/453,341 filed on Mar. 16, 2011. U.S. patent application Ser. No. 13/004,866 is a continuation-in-part of U.S. patent application Ser. No. 12/826,644 and claims the benefit of U.S. Provisional Patent Application No. 61/360,873. This application incorporates by reference all of the above-mentioned patent applications.

FIELD OF THE INVENTION

The invention generally relates to a wound and bandage protection system that is designed to resolve many issues of durability, comfort and ease of application that are not adequately resolved by current wound and bandage protection systems as well as systems for securely holding intravenous tubes and other medical equipment to a patient. The invention also relates to a method of using the wound and bandage protection system for wound care and for securely holding intravenous tubes and other medical equipment to a patient.

BACKGROUND OF THE INVENTION

Throughout the history of bandage making, a common problem has plagued the adhesive bandage industry. In order to properly protect a wound, it should be covered and insulated from outside infectants. However, most adhesive bandages do not adequately protect a wound when applied. Makers of older bandages tried to size the gauze pad to allow for a thin strip of adhesive around the gauze pad to adhere to the skin around the wound. However, the strip of adhesive around the gauze pad would often buckle or come loose altogether, and not keep the wound properly sealed, and possibly cause discomfort. Recently companies have tried other solutions.

Band-Aid® brand has given up on sealing the wound and has extended the gauze to the edge of the adhesive to maximize the amount of gauze available to cover the wound. Nexcare® has created bandages with extremely small gauze in relation to the bandage, allowing for a better seal, but providing less gauze in the exchange. Furthermore, these bandages tend not to perform well on joints, where the areas of adhesive do not conform to the bending of the limbs without causing a large amount of buckling of the gauze. Therefore, there is a need for a bandaging system to prevent buckling and loosening of the adhesive around the gauze pad of an adhesive bandage, particularly with regard to application of bandages to joints, while at the same time maximizing the amount of gauze available to cover the wound.

SUMMARY OF THE INVENTION

The present invention provides a wound/bandage protection system and a method of use thereof. An exemplary embodiment of a super-stretch tube according to the present invention is disclosed. The super-stretch tube has a strip that extends along a length of the super-stretch tube from a first open end to a second open end of the super-stretch tube at least along an inside surface of the super-stretch tube. The super-stretch tube is preferably made of a super-stretchable elastic non-woven material.

According to the present invention, a wound/bandage protector may have a body portion configured as a wrap. On a wound facing side of the body portion proximal to a first end of the body portion is a first catch fastener and on a non-wound facing side of the body portion proximal to a second is a final fastener. The first catch fastener is configured so as to be capable of fastening with a wound facing side of a wound/bandage protector before the final fastener fastens with a non-wound facing side of the wound/bandage protector when wrapping the wound/bandage protector around a limb.

In a first exemplary embodiment of a wound/bandage protector according to the present invention, the wound/bandage protector may be comprised of a body portion, a first-catch fastener and a first fastening tab that acts as a final fastener. The body portion is configured as a wrap with a first end, a second end, a wound facing side and a non-wound facing side. The first-catch fastener is on an end region, which is proximal to the first end of the body portion, of the wound facing side of the body portion. The first-catch fastener is configured so as to be capable of fastening with at least a portion of the non-wound facing side of the body portion. Alternatively, the wound/bandage protector may be configured without the first-catch fastener.

The first fastening strap extends from the second end of the body portion and at least a portion of a wound facing side surface of the first fastening strap is configured so as to be capable of fastening with at least a portion of the non-wound facing side of the body portion or a non-wound facing side of the first fastening strap. In one alternative embodiment, the body portion and the first fastening strap may be comprised of the same integral piece of material.

The wound/bandage protector according to the present invention may be configured to be stretchable in a lengthwise direction defined by the first end of the body portion and the second end of the body portion. The first fastening strap of the wound/bandage protector may have a first strap part that is stretchable, and a second strap part. In such an embodiment of the wound/bandage protector according to the present invention, the second strap part may include the portion of the first fastening strap that is capable of fastening with at least a portion of the non-wound facing side of the body portion or the non-wound facing side of the first fastening strap. An elastic modulus of the first strap part may be greater than an elastic modulus of the body portion.

Furthermore, the wound/bandage protector according to the present invention may also have a second fastening strap extending from the second end of the body portion. At least a portion of a wound facing side surface of the second fastening strap is configured so as to be capable of fastening with at least a portion of the non-wound facing side of the body portion and/or a non-wound facing side of the second fastening strap. The second fastening strap may have a first strap part and a second strap part configured in the manner discussed above in reference to the first fastening strap. An elastic modulus of the second fastening strap first strap part may be configured to be greater than an elastic modulus of the body portion.

The wound/bandage protector according to the present invention may also have a strip. The strip may be on the body portion proximal to the first end and extend widthwise. Alternatively, the strip may extend along the length of the body proximal to a top or bottom edge of the body portion. Moreover, multiple strips may be provided, such as strips along both the top and bottom edge of the body portion. The strip may be comprised of a rubberized material exposed on at least the wound facing side of the body portion.

The wound/bandage protector according to the present invention may have a gauze port on the wound facing side of the body portion proximal to the first end of the body portion. The gauze port may be configured to attach to only a small portion of a gauze pad proximal to one side of the gauze pad. The gauze port may be configured so as to allow repeated removable attachment of the gauze pad. The wound/bandage protector may also include a gauze pad. The gauze pad may be configured to attach to the gauze port. Alternatively, the gauze pad may be configured so as to remain adjacent but unattached to the non-wound facing side of the body portion. In such an alternative exemplary embodiment, the gauze pad may have a rubberized or tacky frame on a wound-facing and/or non-wound-facing side of the gauze pad.

The wound/bandage protector according to the present invention may have a strip provided on the body portion preferably between the gauze port and the first end of the body portion. If there is no gauze port, the strip is preferably located proximal to the first end of the body portion. The strip may be comprised of a rubberized material that is exposed at least on the wound facing side of the body portion. Alternatively, all or a portion of the wound-facing side of the body portion may have a tacky surface.

A wound/bandage protector according to the present invention, may have a cover. In such an embodiment of the wound/bandage protector according to the present invention, the body portion has an aperture, and the cover and the aperture are sized so as to allow the cover to completely close the aperture. The body portion may be configured with a shelf surrounding the aperture, and the cover is sized so as to close the aperture by extending at least partially onto the shelf. The wound/bandage protector according to this exemplary embodiment may further comprise a non-stretchable or substantially non-stretchable rim provided on the non-wound-facing side surface of the body portion surrounding the aperture. The surface of the rim is sized and configured so as to allow for removable attachment of the cover.

A wound/bandage protector according to the present invention, may have dead-zones periodically provided along the length of the body portion. The dead zones may be configured to extend widthwise with respect to the length of the bandage and provided, preferably, at least every 3 inches along the length of the body portion.

A wound/bandage protector according to the present invention, may have a gauze panel positioned on or integrated into the body portion proximal to the first end of the body portion.

The gauze panel may be configured so as to allow for attachment and/or repeated attachment of a gauze pad on the wound-facing side of the body portion. The gauze panel may be sized so as to allow all or substantially all of the gauze pad to be attached or removably attached to the gauze panel. The gauze panel and the part of the body portion on which the gauze panel is positioned or integrated may be configured as a dead zone. Alternatively, the gauze pad and the gauze panel may be comprised of stretchable material.

In one exemplary embodiment of a bandage according to the present invention, the bandage is comprised of a stretchable body portion with a stretchable gauze pad affixed to the wound-facing side of the body portion. The body portion has adhesive on at least a portion of a wound facing side or, alternatively, the body portion is comprised of self adherent material, such as Coban™.

The present invention also discloses methods of protecting wounds using the wound/bandage protectors, bandages and super-stretch tubes, such as the exemplary embodiments of those disclosed herein. Thus, for example, a bandage with an aperture may be used to protect a wound by applying the bandage with the aperture opened, placing gauze and medicine on the wound; and closing the aperture of the bandage. The method may also be applied with wound/bandage protector with an aperture. Similarly with all the bandages and wound/bandage protectors disclosed herein, the bandage or wound/bandage protector may first be placed over the wound and then a wound/bandage protector or super stretch tube may be positioned over the bandage or wound/bandage protector. In addition, the invention also relates to a kit that includes all or a set of the wound/bandage protectors, bandages, and/or super-stretch tubes, as disclosed herein.

BRIEF DESCRIPTION OF THE DRAWINGS

FIG. 19A is a bottom-side view of an exemplary embodiment of a wound/bandage protector accessory holder;

FIG. 19B is a top-side view of an exemplary embodiment of a wound/bandage protector accessory holder;

FIG. 20A is a side view of the wound/bandage protector of FIG. 6C, illustrating only the relevant elements thereof, before the wound/bandage protector is fastened to a limb;

FIG. 20B is the side view of the wound/bandage protector as shown in FIG. 6C fastened to the limb via a first catch fastener fastened with a wound facing side of a body portion, with a portion of a fastening strap not fastened with a non-wound facing side of the body portion and with the wound/bandage protector accessory holder mounted on a non-wound facing side of the body portion;

FIG. 20C is a side view of the wound/bandage protector with the wound/bandage protector accessory holder as shown in FIG. 20B with a portion of a fastening strap fastened with a non-wound facing side of the body portion;

FIG. 21 shows a perspective view of the wound/bandage protector accessory holder mounted on the non-wound facing side of the body portion;

FIG. 22A is a bottom-side view of a second exemplary embodiment of a wound/bandage protector accessory holder;

FIG. 22B is a top-side view of a second exemplary embodiment of a wound/bandage protector accessory holder;

FIG. 23 shows a perspective view of the wound/bandage protector accessory holder in an exemplary process of being mounted to the non-wound facing side of the body portion;

FIG. 24A is a side view of another exemplary embodiment of a wound/bandage protector, according to the present invention;

FIG. 24B is a top cross-sectional view of the wound/bandage protector illustrated in FIG. 24A taken along line 2*e*-2*e*' with a strap in an open position;

FIG. 24C is a top cross-sectional view of the wound/bandage protector illustrated in FIG. 24A with the strap portion in a closed position;

FIG. 25A is a top-side a view of an exemplary accessory holder according to the present invention;

FIG. 25B is a bottom-side view of an exemplary accessory holder according to the present invention;

FIG. 25C is a side view of the exemplary accessory holder of FIGS. 25A and 25B with a first tube or wire configuration;

FIG. 25D is a side view of the exemplary accessory holder of FIGS. 25A and 25B with a second tube or wire configuration;

FIG. 26A is a side view of the wound/bandage protector of FIG. 6C, illustrating only the relevant elements thereof, before the wound/bandage protector is fastened to a limb;

FIG. 26B is the side view of the wound/bandage protector as shown in FIG. 6C fastened to the limb via a first catch fastener fastened with a wound facing side of a body portion, with a final fastener not fastened with a non-wound facing side of the body portion;

FIG. 26C is a side view of the wound/bandage protector of FIG. 6C with a final fastener fastened with a non-wound facing side of the body portion;

FIG. 27A is a side view of the wound/bandage protector of FIG. 7C, illustrating only the relevant elements thereof, before the wound/bandage protector is fastened to a limb;

FIG. 27B is the side view of the wound/bandage protector as shown in FIG. 7C fastened to the limb via a first catch fastener fastened with a wound facing side of a body portion, with a final fastener not fastened with a non-wound facing side of the body portion;

FIG. 27C is a side view of the wound/bandage protector of FIG. 7C with a final fastener fastened with a non-wound facing side of the body portion;

FIG. 28A is a side view of the wound/bandage protector of FIG. 8C, illustrating only the relevant elements thereof, before the wound/bandage protector is fastened to a limb;

FIG. 28B is the side view of the wound/bandage protector as shown in FIG. 8C fastened to the limb via a first catch fastener fastened with a wound facing side of a body portion, with a final fastener not fastened with a non-wound facing side of the body portion;

FIG. 28C is a side view of the wound/bandage protector with a final fastener fastened with a non-wound facing side of the body portion;

DETAILED DESCRIPTION OF THE INVENTION

Figure 1A:
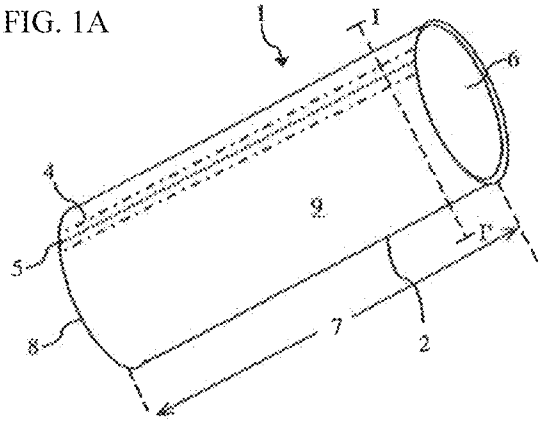
FIG. 1A is a perspective side view of an exemplary embodiment of a super-stretch tube according to the present invention.
Figure 1B:
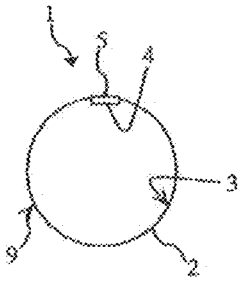
FIG. 1B illustrates an exemplary embodiment of a cross-sectional view of the super-stretch tube taken along the line I-I' in FIG. 1A.

FIGS. 1A and 1B show a super-stretch tube 1 that is part of the bandaging system according to the present invention. The super-stretch tube 1 may be used for protecting a wound or for covering one of the bandages disclosed below. The super-stretch tube 1 has a tube body portion 2 which may be made of a stretchable material such as an elastic non-woven that is found in the side portions of Huggies® brand Little Swimmers® and Pull-Ups® or Pampers® Easy Ups® Cruisers®. Alternatively, the tube body portion 2 may be made of other materials with similar elasticity properties that provide a comparable amount of stretchability and tension.

According to one exemplary embodiment of the invention, the stretchable material of the tube body portion 2, when extended to its full capacity, can stretch to more than double the tube body portion's 2 un-extended size. In the context of this application, "super stretchable" material refers to material that can resiliently stretch to a length that is equal to or greater than one and a half times the length of the material when not under tension. In the context of this application, "stretchable" material refers to material that can resiliently stretch to a length that is at least ten percent greater than the length of the material when not under tension. A material that has "little or no stretch" is one that is not super stretchable. A material that has "no stretch" is one that is not stretchable. A "dead zone" is an area of material that has little or no stretch which may, but not necessarily, be an integral part of an otherwise stretchable material. A dead zone area may be formed in an elastic nonwoven material with an ultrasonic seal, which is generally used when attaching two nonwovens together, by punching, applying pressure and then high frequency vibration, which causes nonwoven materials to melt, to an overlapping connecting portion of the two nonwovens. Alternatively, particularly when forming a dead zone in a single piece of nonwoven fabric, the dead zone may be formed by simply applying the pressure and high frequency vibration without punching. The "stretching resistance", "elastic modulus" or Young's modulus, refers to a ratio of stretching force on a particular area along a particular axis over a ratio of change in the length of the material along the particular axis due to the applied stretching force. Thus, a material that can be "easily" stretched has a lower elastic modulus than a material that is "hard" to stretch. The stretchable material of the tube body portion 2 at least provides stretching capacity in a manner that allows a circumference of the super-stretch tube 1 to vary. The stretchable material of the tube body portion 2 may, alternatively, provide stretching capacity that allows both the circumference and a length of the tube body portion 2 to vary. Preferably, the super-stretch material of the tube body portion 2 is very thin, being less than $1/16^{th}$ of an inch thick when in the un-extended position and provides some breathability as well as good water resistance.

The super-stretch tube 1 has a strip 4 that extends along a length 7 of the super-stretch tube 1 from a first open end 6 of the super-stretch tube 1 to a second open end 8 of the super-stretch tube 1 at least along an inside surface 3 of the super-stretch tube 1. The strip 4 may be positioned along or over a seam 5 that may extend the length of the super-stretch tube 1. The strip 4 has one or more threads made of a rubberized material provided in such a manner that the rubberized material threads are exposed at least on an inner side of the super-stretch tube 1. The strip 4 may be made from an elastic material used in some larger hair bands that includes rubberized material threads. The rubberized material is not necessarily exposed on the exterior side 9 of the stretch tube 1. Alternatively, the strip 4 may be comprised of stretch non-slip medical grade silicone or similar, preferably latex free, material. The non-slip silicone may be applied in a continuous or discontinuous manner to form the strip 4. Alternatively, the entire inside of the tube may be coated with low tack non-slip silicone or similar, preferably latex free, material.

Although not depicted in FIGS. 1A and 1B of the super-stretch tube 1, in an alternative exemplary embodiment of the super-stretch tube 1 according to the present invention, there may also be one or more super-stretch tube fastening straps attached to an exterior surface 9 of the super-stretch tube 1. The one or more super-stretch tube fastening straps may be configured in a similar fashion as fastening strap 23 shown in FIGS. 2A and 2B and discussed below. Preferably, a first fastening strap of the one or more super-stretch tube fastening straps may be provided in close proximity to the first open end 6 of the super-stretch tube 1 and a second fastening strap of the one or more of the super-stretch tube fastening straps may be provided in close proximity to the to the second open end 8 of the super-stretch tube 1.

Figure 2A:
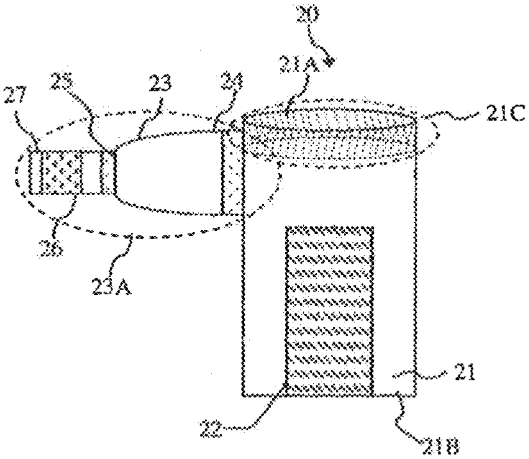
FIG. 2A is a side view of an exemplary embodiment of a wound/bandage protector according to the present invention.

FIG. 2A shows an exemplary embodiment of a wound/bandage protector 20, according to the present invention. The wound/bandage protector 20 is configured as a "sock/mitten", with a body 21 that has a first end 21A that is open and a second end 21B that is closed. The body 21 may be made of super-stretchable or stretchable material similar to the material of the super-stretch tube 1, discussed above and shown in FIGS. 1A and 1B and at least a portion of the non-wound facing side of the body 21 may be configured as a Velcro® loop type fastener. The stretchable material of the body 21 of the wound/bandage protector 20 at least provides such stretching capacity in a manner that allows a circumference of the body 21 to vary. The stretchable material of the body 21 may, alternatively, provide such stretching capacity that allows both the circumference and a length of the body 21 to vary.

The body 21 has a panel 22 which may be made of material that has little or no stretch. The panel 22 is shown in FIG. 2A, which illustrates an outside side view showing a portion of an external non-wound facing surface of the wound/bandage protector 20. However, the panel 22 is not necessarily visibly distinguishable from the rest of the body 21, particularly on the external non-wound facing surface of the wound/bandage protector 20. A gauze pad (not specifically illustrated in FIG. 2A may be affixed to the panel 22 on an internal wound-facing side. Alternatively, the gauze pad may be attached to the panel 22 in a temporary fashion such as via use of a Velcro® type fastening system or a reusable pressure sensitive adhesive such as that used in Post-It® notes. In another alternative embodiment, the panel 22 and the gauze pad is made of stretchable or super-stretchable material. In this embodiment, the entire body 21 may be configured to function as the panel 22.

In the context of this specification, gauze, or gauze pad, refers to any material or composite of material that may be therapeutically used as a pad over a wound. For example, the gauze pad may be made of cotton or a polyester blend fabric. The fabric may be covered with a plastic porous film such as Telfa® which prevents or minimizes wound adhesion. Furthermore, the gauze pad may be backed with a film that prevents body fluids from penetrating through the gauze pad to the bandage.

The body 21 has an external non-wound facing surface and an internal wound-facing surface. Attached to the external non-wound facing surface of the body 21 proximate to the first end 21A is a fastening strap 23A. The fastening strap 23A, as illustrated in FIG. 2A has a first strap part 23 that may be attached to the body 21 via a first attachment region 24. The first strap part 23 may be comprised of a stretchable or super stretchable material similar to the material used in the super-stretch tube 1. The material of the first strap part 23 preferably provides a stretching resistance that is greater than the stretching resistance of the body 21. The material of the first strap part 23 at least provides such stretching capacity in a manner that allows the length of the fastening strap 23A to vary. The first attachment region 24 is preferably configured as a dead zone to provide no stretch and may be comprised of a composite of the material of the first strap part 23 and the body 21 of the wound/bandage protector 20 and may be attached by a punch and melt heat seal. Alternatively, the first strap part 23 is directly attached to the body 21 without the first attachment region 24 intervening therebetween.

A second strap part 27 is attached to the first strap part 23 via a second attachment region 25. The second attachment region 25 is preferably configured as a dead zone to provide no stretch and may be comprised of a composite of the material of the first strap part 23 and the second strap part 27 and may be attached by a punch and melt heat seal. Alternatively, the second strap part 27 is directly attached to the first strap part 23 without the second attachment region 25 intervening therebetween. The fastening strap 23A has a wound facing side, which may be seen in FIG. 2A. The second strap part 27 has a portion 26 that includes a Velcro® hook type material, such as Velcro® USA HTH 819 natural, on a wound-facing side of the fastening strap 23A. Alternatively, the second strap part 27 or the entire fastening strap 23A may be comprised of a cohesive material such as Coban™ so that the fastening strap 23A when wrapped around can fasten to itself.

On the internal wound-facing surface of the of the body 21 proximate to the first end 21A is a strip 21C, which may be similar in configuration to the strip 4 in the super-stretch tube 1, having one or more threads made of a rubberized material that provides a moderate amount of friction interwoven in the strip 21C in such a manner that the rubberized material threads are exposed. Alternatively, the strip 21C may be made of stretch non-slip silicone or similar, preferably latex free, material that provides a frictional surface. The non-slip silicone may be applied in a continuous or discontinuous manner to form the strip 21C. Preferably, the amount of friction provided by the frictional surface of the strip 21C should be one that does not cause discomfort when the wound/bandage protector 20 is worn. For purposes of this application indication of "rubberized material" without further limitation refers to any material that provides a frictional surface, including non-slip silicone and Coban™.

Figure 2B:
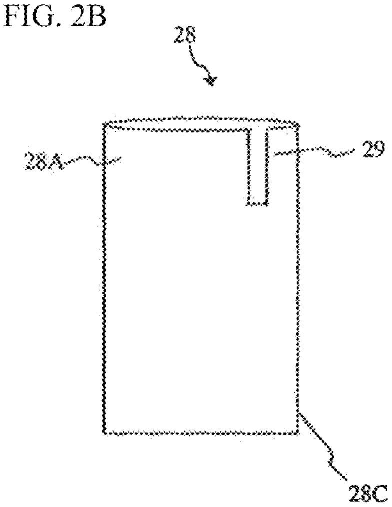
FIG. 2B is a side view of an exemplary embodiment of a protective sheath for the wound/bandage protector illustrated in FIG. 2A.
Figure 2C:
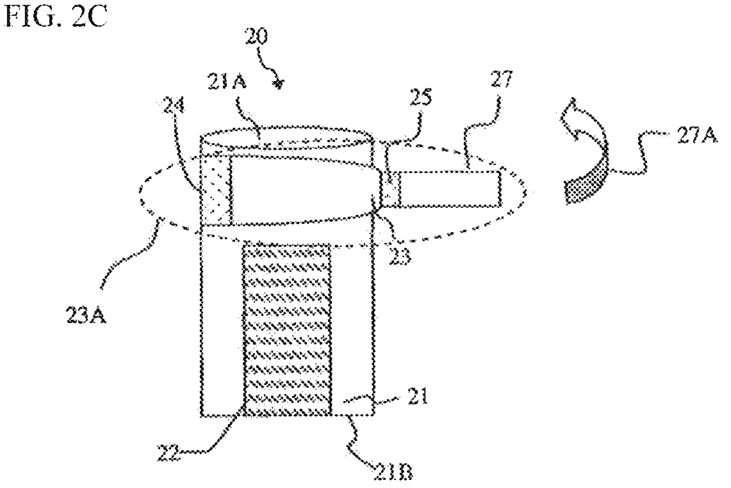
FIG. 2C is a side view of the exemplary embodiment of the wound/bandage protector illustrated in FIG. 2A illustrating the process of securing the wound/bandage protector.

FIG. 2C illustrates the process of securing the wound/bandage protector 20 of FIG. 2A by showing the fastening strap 23A in an intermediate position, as the fastening strap 23A is being extended around the external non-wound facing surface of the wound/bandage protector 20 in the direction indicated by arrow 27A. The fastening strap 23A has a non-wound facing side, which may be seen in FIG. 2C. The first strap part 23 may be configured to act as a loop portion of a Velcro® type fastener on the non-wound facing side of the first strap part 23. The second strap part 27 may be configured as a loop portion of a Velcro® type fastener on the non-wound facing side of the fastening strap 23A.

The wound/bandage protector 20 may be slipped onto an appendage through the opening on the first end 21A of the body 21 so that the gauze pad that is affixed to the panel 22 of the wound/bandage protector 20 covers a wound on the appendage, and the wound/bandage protector 20 is then secured in place by wrapping the fastening strap 23A around the outside of the wound/bandage protector 20 and affixing the Velcro® hook fastener portion 26 of the second strap part 27 to the loop portion of the first strap part 23, the body 21, or the loop portion of the second strap part 27.

Figure 2D:
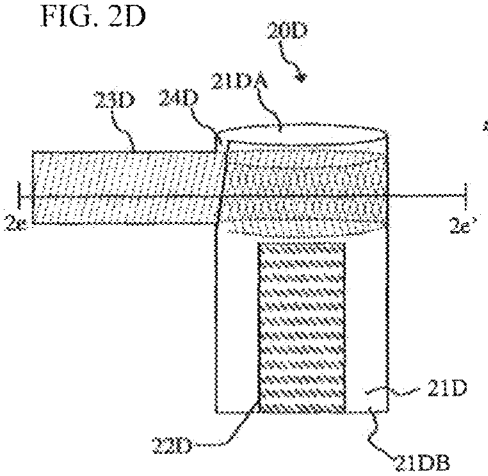
FIG. 2D is a side view of an exemplary embodiment of a wound/bandage protector according to the present invention.
Figure 2E:
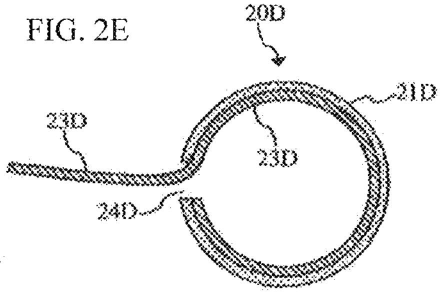
FIG. 2E is a top cross-sectional view of the wound/bandage protector illustrated in FIG. 2D taken along line 2*e*-2*e*' with a strap in an open position.
Figure 2F:
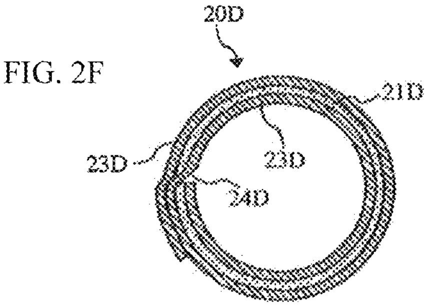
FIG. 2F is a top cross-sectional view of the wound/bandage protector illustrated in FIG. 2D with the strap portion in a closed position.

FIG. 2D shows another exemplary embodiment of a wound/bandage protector 20D, according to the present invention, that is configured as a "sock/mitten". The wound/bandage protector 20D has a body 21D that may be configured as described above for the body 21. The body 21D has a first end 21DA that is open and a second end 21DB that is closed and a panel 22D where a gauze pad may be permanently or detachably affixed. The wound/bandage protector 20D, however, has a strap 23D located proximate to the first end 21DA that is comprised of a cohesive material such as Coban™. The strap 23D, instead of attaching to an external non-wound facing surface of the body 21D, extends through a slit 24D that allows the strap 23D to extend onto an internal wound-facing surface of the body 21D. FIG. 2E is a top cross-sectional view taken along the line 2*e*-2*e*' illustrating how the strap 23D attaches to the internal wound-facing surface of the body 21D and extends entirely around a circumference of the body 21D or alternatively around a portion of the circumference. FIGS. 2D and 2E illustrate the wound/bandage protector 20D with the strap 23D in an open position. FIG. 2F illustrates a top cross-sectional view of the wound/bandage protector 20D in a closed position. As is illustrated, the portion of the strap 23D that is not attached to the internal wound-facing side of the body 21D is of sufficient length to extend around the outside circumference of the wound/bandage protector 20D and to overlap on itself so as to securely affix the strap 23D to itself. Alternatively, a portion of the outside circumference of the wound/bandage protector 20D may be covered with the cohesive material so that the strap 23D can securely fasten to the outside circumference of the wound/bandage protector 20D rather than having the strap 23D extending around onto itself.

FIG. 24A shows another exemplary embodiment of a wound/bandage protector 20E, according to the present invention, that is configured as a "sock/mitten". The wound/bandage protector 20E has a body 21E that may be configured as described above for the body 21. The body 21E has a first end 21EA that is open and a second end 21EB that is closed and a panel 22E where a gauze pad may be permanently or detachably affixed. The wound/bandage protector 20E, however, has a strap 23E located proximate to the first end 21EA. The strap 23E, instead of attaching to an external non-wound facing surface of the body 21E, extends through a slit 24E that allows the strap 23E to extend onto an internal wound-facing surface of the body 21E. As illustrated, the slit 24E extends all the way to the first end 21EA, alternatively the slit 24E may not extend all the way to the first end 21EA. The strap 23E does not extend all the way to the first end 21EA leaving a flap-over portion 723. FIG. 24B is a top cross-sectional view taken along the line 72*e*-72*e*' illustrating how the strap 23E attaches to the internal wound-facing surface of the body 21E and extends entirely around a circumference of the body 21E or alternatively around a portion of the circumference of the internal wound-facing surface of the body 21E. The wound facing side 23EA of the strap 23E that is internal to the body 21E is configured as/or with a non-slip grip surface 722 that may be configured and functions similar to the strip 21C. The portion of the strap 23E that is external to the body 21E may extend entirely or partially around an external circumference of the body 21E. The wound facing side 23EA of the strap 23E that is external to the body 21E is configured as/or with a fastener 721 so that the strap 23E may be fastened to the external circumference of the body 21E. Alternatively, the portion of the strap 23E that is external to the body 21E may be of sufficient length to extend around the outside circumference of the body 21E and to overlap onto itself and is configured as/or with the fastener 721 so that the strap 23E may be securely affixed to wound facing side 23EB of the strap 23E. FIGS. 24A and 24B illustrate the wound/bandage protector 20E with the strap 23E in an open position. FIG. 24C illustrates a top cross-sectional view of the wound/bandage protector 20E in a closed position. After the wound/bandage protector 20E is placed on a limb and the strap 23E is fastened, the flap-over portion 723 may be folded over the strap 23E such that the flap-over portion 723 may partially or fully cover the strap 23E or even extend further than the strap 23E. Thus as illustrated in FIG. 24C the flap-over portion 723 of the body 21E also forms an outer layer of the cross-section. In an alternative embodiment, the strap 23E may extend to the first end 21EA and the strap 23E may be folded over onto itself or completely flipped over along with the flap-over portion 723. Alternatively the flap-over portion 723 may extend further downward toward the second end 21EB and the strap 23E may be folded over onto itself or completely flipped over along with the flap-over portion 723. Additionally, with regard to the wound/bandage protector 20D, the same method of fastening with a flap-over portion and the related structural variations may be applied.

Figure 3A:
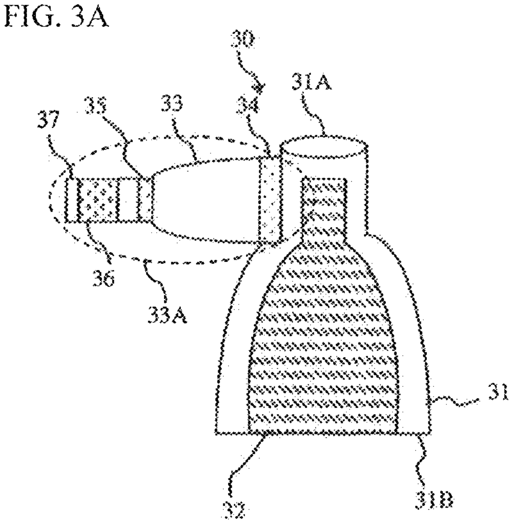
FIG. 3A is a side view of an exemplary embodiment of a wound/bandage protector according to the present invention.

FIG. 3A shows an exemplary embodiment of a wound/bandage protector 30, according to the present invention. The wound/bandage protector 30 is configured as a sock/mitten similar to the wound/bandage protector 20 in FIG. 2A. The wound/bandage protector 30 has a body 31 that has a first end 31A that is open and a second end 31B that is closed. However, the body 21 of the wound/bandage protector 20 has a uniform circumference from the open end 21A to the closed end 21B and a panel 22, which has a uniform width. In contrast, the body 31 of the wound/bandage protector 30 is tapered from the open end 31A to the closed end 31B so that one end is larger than the other, and a panel 32 is also tapered. Alternatively, the panel 32 may also have a uniform width, regardless of the shape or circumference of the body 31. The body 31 and the panel 32 are otherwise similarly configured to the body 21 and the panel 22.

The body 31 has an external non-wound facing surface and an internal wound-facing surface. Attached to the external non-wound facing surface of the body 31 proximate to the first end 31A is a fastening strap 33A. The fastening strap 33A has a first strap part 33, a second strap part 37, a portion 36 of the second strap part 37, a first attachment region 34 and a second attachment region 35 that are configured similar to the corresponding components of the fastening strap 23A in FIG. 2A.

Figure 3B:
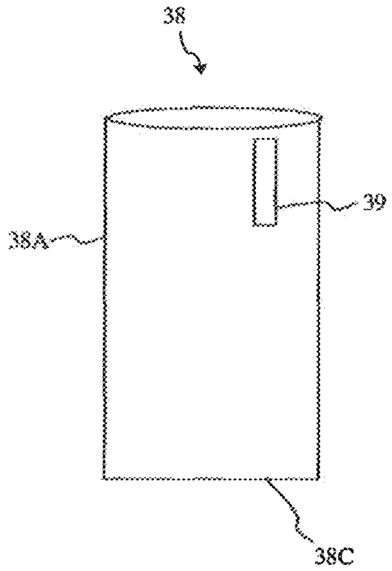
FIG. 3B is a side view of an exemplary embodiment of a protective sheath for the wound/bandage protector illustrated in FIG. 3A.

FIG. 2B illustrates a first alternative embodiment of a protective sheath 28 and FIG. 3B illustrates a second alternative embodiment of a protective sheath 38. Both the protective sheath 28 and the protective sheath 38 may each be used in conjunction with either the wound/bandage protector 20 or the wound/bandage protector 30. Each of the protective sheaths 28, 38 has a body 28A, 38A with an opening on a first end 28B, 38B and a second end 28C, 38C that is closed. The bodies 28A, 38A are configured to fit snugly over the exterior of the wound/bandage protector 20, 30. The bodies 28A, 38A may be comprised of a waterproof or water resistant material such as the plastic material used in Playtex® bottle liners or vinyl, or a waterproof or water resistant non-woven material, and may be configured with a plastic backing and/or with the capability of being stretchable or super stretchable. Alternatively, the bodies 28A, 38A may be comprised of a composite of materials, preferably one that will provide a waterproof or water-resistant barrier. The protective sheath 28 has a slit 29 and the protective sheath 38 has a slot 39. Both the slit 29 and the slot 39 are sized and positioned to allow the fastening strap 23A, 33A of the wound/bandage protector 20,30 to fit through so that the fastening strap 23A, 33A can extend around the outside of the sheath and secure both the wound/bandage protector 20,30 as well as the sheath to an appendage being bandaged. On the wound facing side of the fastening strap 23A, 33A may be a tacky surface, which may be comprised of a pressure sensitive adhesive, or rubberized surface, or self-adherent surface material with a corresponding self-adherent surface material on the protective sheath 28,38. Preferably, the tacky surface of the fastening strap 23A, 33A is on the first and/or second attachment regions 24, 34 and 25, 35.

Figure 4:
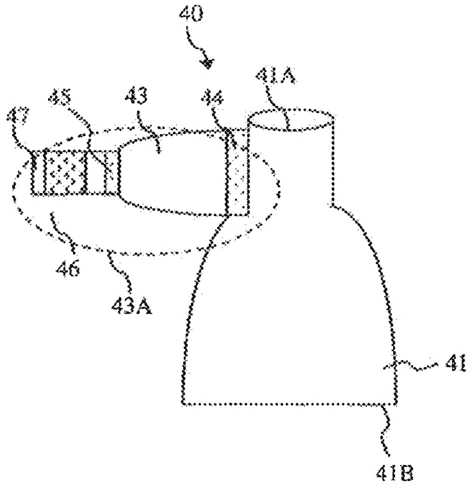
FIG. 4 is a side view of an exemplary embodiment of a wound/bandage protector according to the present invention.

FIG. 4 shows an exemplary embodiment of a wound/bandage protector 40 according to the present invention. The wound/bandage protector 40 is configured as a sock/mitten similar to the wound/bandage protector 30 in FIG. 3A. The wound/bandage protector 40 has a body 41 that has a first end 41A that is open and a second end 41B that is closed. However, the wound/bandage protector 30 has a panel 32 whereas the wound/bandage protector 40 does not have a panel.

The body 41 is otherwise similarly configured to the body 31. The body 41 has an external non-wound facing surface and an internal wound-facing surface. Attached to the external non-wound facing surface of the body 41 proximate to the first end 41A is a fastening strap 43A. The fastening strap 43A has a first strap part 43, a second strap part 47, a portion 46 of the second strap part 47, a first attachment region 44 and a second attachment region 45 that are configured similar to the corresponding components of the fastening strap 33A in FIG. 3A.

The wound/bandage protector 40 may be slipped onto an appendage through the wound/bandage protector opening 41A so that it covers a wound or a bandage on the appendage, or another wound/bandage protector such as the exemplary embodiments in FIGS. 2A and 3A. The wound/bandage protector 40 is then secured in place by wrapping the fastening strap 43A around the outside of the wound/bandage protector 40 and affixing the Velcro® hook fastener portion 46 of the second strap part 47 to the loop portion of the first strap part 43, the body 41 or the loop portion of the second strap part 47.

Figure 5:
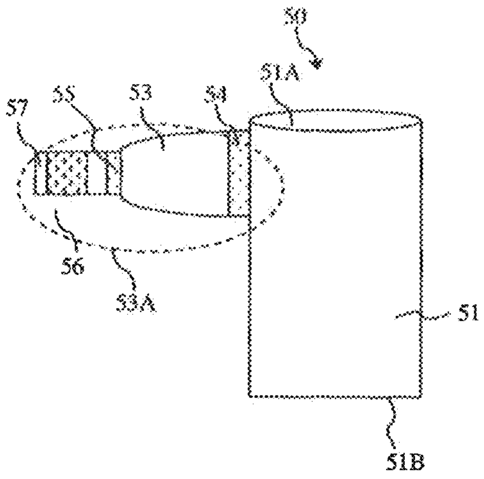
FIG. 5 is a side view of an exemplary embodiment of a wound/bandage protector according to the present invention.

FIG. 5 shows an exemplary embodiment of a wound/bandage protector 50 according to the present invention. The wound/bandage protector 50 is configured as a sock/mitten similar to the wound/bandage protector 20 in FIG. 2A. The wound/bandage protector 50 has a body 51 that has a first end 51A that is open and a second end 51B that is closed. However, the wound/bandage protector 20 has a panel 22 whereas the wound/bandage protector 50 does not have a panel.

The body 51 is otherwise similarly configured to the body 21. The body 51 has an external non-wound facing surface and an internal wound-facing surface. Attached to the external non-wound facing surface of the body 51 proximate to the first end 51A is a fastening strap 53A. The fastening strap 53A has a first strap part 53, a second strap part 57, a portion 56 of the second strap part 57, a first attachment region 54 and a second attachment region 55 that are configured similar to the corresponding components of the fastening strap 23A in FIG. 2A.

The wound/bandage protector 50 may be slipped onto an appendage through the wound/bandage protector opening 51A so that it covers a wound or a bandage on the appendage, or another wound/bandage protector such as the exemplary embodiments in FIGS. 2A and 3A, and the wound/bandage protector 50 is then secured in place by wrapping the Velcro® stretch strap around the outside of the wound/bandage protector 50 and affixing the Velcro® hook fastener portion 56 of the second strap part 57 to the loop portion of the first strap part 53, the body 51 or the loop portion of the second strap part 57.

Figure 6A:
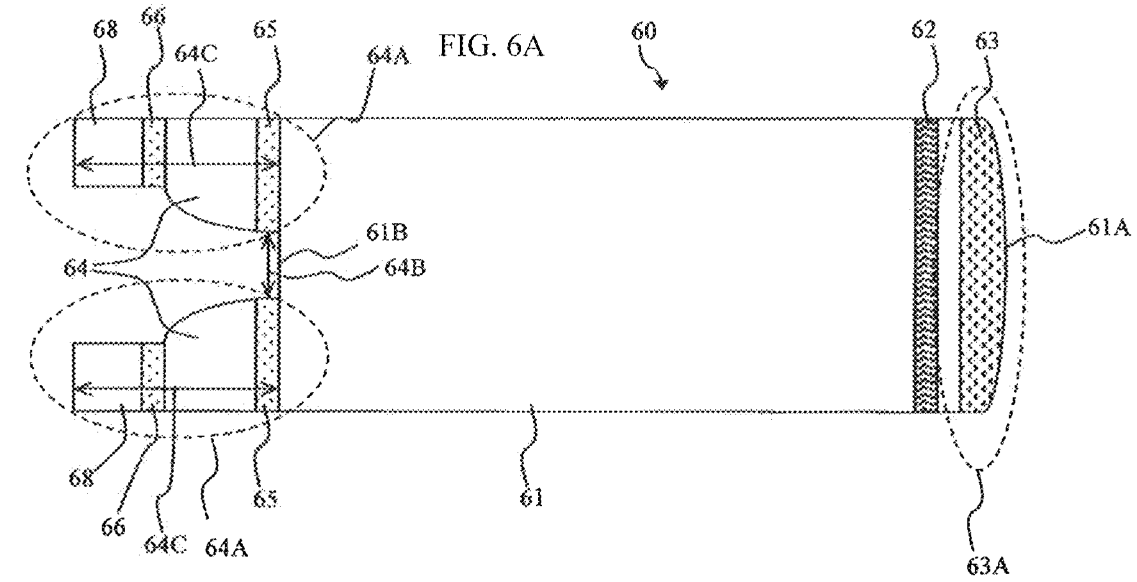
FIG. 6A is a top non-wound facing side view of an exemplary embodiment of a wound/bandage protector according to the present invention.
Figure 6B:
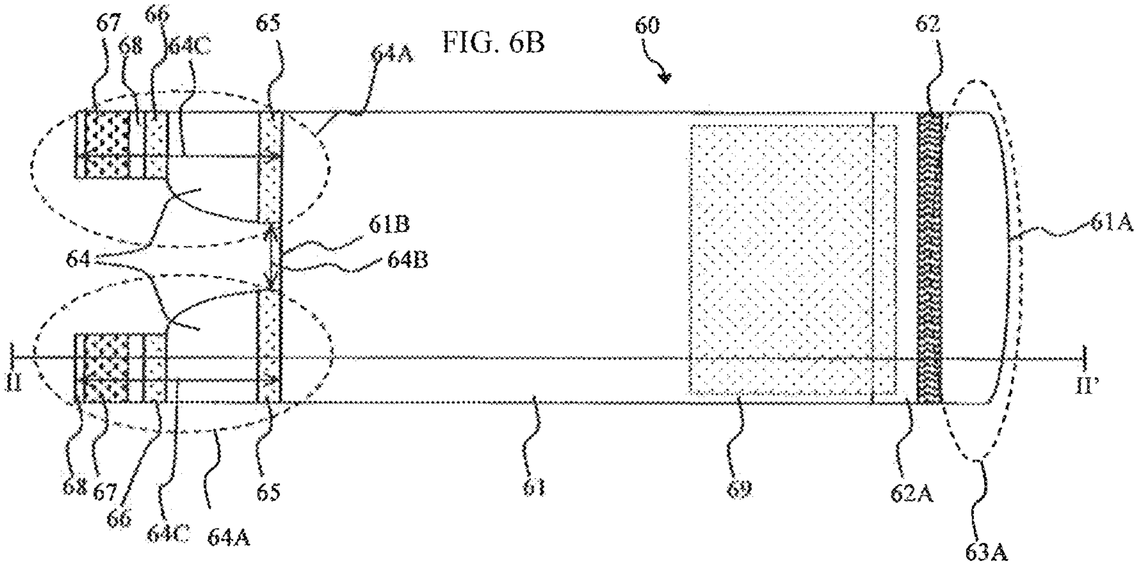
FIG. 6B is a bottom wound facing side view of the exemplary embodiment of the wound/bandage protector illustrated in FIG. 6A.
Figure 6C:
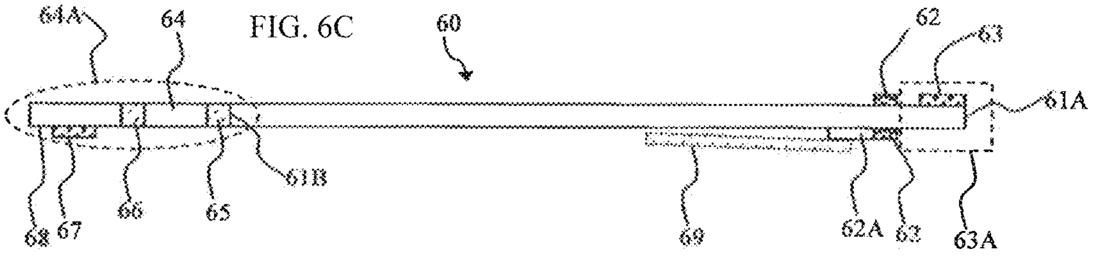
FIG. 6C is a side cross-sectional view of the exemplary embodiment of the wound/bandage protector illustrated in FIGS. 6A and 6B taken along the line II-II' in FIG. 6B.

FIGS. 6A to 6C are, respectively, a top non-wound-facing view, a bottom wound facing view, and a cross-sectional side view taken along the line II-II' of a wound/bandage protector 60 according to the present invention. The exemplary embodiment of the wound/bandage protector 60 has a body portion 61 that is configured as a wrap which may be comprised of super-stretch material similar to the super-stretch material used in the body 21, 31 of the bandage mittens/socks 20, 30. The body portion 61 is configured to act as a loop portion of a Velcro® type fastener on both the bottom wound-facing side of the wound/bandage protector 60 and the top non-wound facing side of the wound/bandage protector 60. The body portion 61 has a length that runs from a first end 61A to a second end 61B. The stretchable material of the body portion 61 at least provides such stretching capacity in a manner that allows the length of the body portion 61 to vary. The stretchable material of the body portion 61 may, alternatively, provide such stretching capacity that allows both the length of the body portion 61 as well as a width of the body portion 61 which is perpendicular to the length of the body portion 61 to vary.

A gauze port 62A is positioned on or integrated into the body portion 61 proximal to the first end of the body portion 61A. The gauze port 62A is an area where a gauze pad 69 may be attached or removably attached to the wound-facing side of the body portion 61. The gauze port 62A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, both the gauze port 62A and the gauze pad 69 may have a low tack adhesive, such as a low tack silicone adhesive. The low tack adhesive may be on the entire non-wound facing side of the gauze pad 69, or may be just on a portion of the non-wound facing side of the gauze pad 69. Another possibility is that the surface of the gauze port 62A may be comprised of an adhesive that allows for the permanent attachment of the gauze pad 69. The gauze port 62A may be used to attach different sized gauze pads 69 as well as to periodically replace the gauze pad 69 in the wound/bandage protector 60 shown in this embodiment. The gauze port 62A may be sized and/or configured so as to attach to all, a substantial portion, or a small portion as illustrated in the FIGS. 6B and 6C, such as one side of the gauze pad 69.

In closer proximity to the first end 61A of the body portion 61 of the wound/bandage protector 60 than the gauze port 62A, is a strip 62, which may be similar in configuration to the strip 4 in the first embodiment, having one or more threads made of a rubberized material that provides a moderate amount of friction interwoven in the strip 62 in such a manner that the rubberized material threads are exposed. Alternatively, the strip 62 may be made of stretch non-slip silicone or similar, preferably latex free, material that provides a frictional surface. The non-slip silicone may be applied in a continuous or discontinuous manner to form the strip 62. Preferably, the amount of friction provided by the frictional surface of the strip 62 should be one that does not cause discomfort when the wound/bandage protector 60 is worn. The strip 62 could be configured so that it is not stretchable in either one or both of the length or the width directions. The strip 62 may be provided along the top non-wound facing side of the wound/bandage protector 60 and/or the bottom wound facing side of the wound/bandage protector 60. Moreover, the strip 62 may extend around sides of the wound/bandage protector 60 and along both the top non-wound facing side of the wound/bandage protector 60 and the bottom wound facing side of the wound/bandage protector 60 so as to form an annular shape.

A region 63A of the body portion 61 extends from the strip 62 to the first end of the body portion 61. On the end region 63A of the first end of the body portion 61A, although not necessarily on the entire end region 63A, is a first-catch fastener 63 on the top non-wound-facing side of the wound/bandage protector 60. The first-catch fastener 63 is configured so as to be capable of fastening with at least a portion of the wound facing side of the body portion 61. The first end of the body portion 61A may be curved as shown in FIGS. 4A and 4B or straight or any other configuration.

Attached to the second end of the body portion 61B are two fastening tabs 64A. Each of the fastening tabs 64A may be comprised of two parts. A first tab part 64 is attached to the second end of the wound/bandage protector body portion 61B and is made out of a super-stretch material which may be adapted to function as a loop portion of a Velcro®-type fastener on both the top non-wound facing side and the bottom wound-facing side of the wound/bandage protector 60. The super-stretch material of the first tab part 64 preferably provides a stretching resistance that is greater than the stretching resistance of the body portion 61. The first tab part 64 may be attached to the second end of the wound/bandage protector body portion 61B via an attachment region 65 which is preferably configured as a dead zone to provide no stretch. The attachment region 65 may be comprised of a composite of the material of the first tab part 64 and the body portion 61 of the wound/bandage protector 60 and may be attached by a punch and melt heat seal. Alternatively, the first tab part 64 is directly attached to the body portion 61 without an attachment region 65 intervening therebetween.

A second tab part 68 is attached to the first tab part 64 via an attachment region 66. The attachment region 66 is preferably configured as a dead zone to provide no stretch and may be comprised of a composite of the material of the first tab part 64 and the second tab part 68 and may be attached by a punch and melt heat seal. The second tab part 68 has a final fastener 67 which includes a Velcro® hook type material on the bottom wound-facing side of each of the fastening tabs 64A. Alternatively, the second tab part 68 is directly attached to the first tab part 64 without an attachment region 66 intervening therebetween. There may be a spacing 64B between inner sides of the two fastening tabs 64A at the second end of the wound/bandage protector body portion 61B. The shape of the inner sides of the two fastening tabs 64A may be comprised of an arc, an arc combined with a straight line, an angled line, or any other embodiment which would allow for a distance between the two inner sides of the two fastening tabs 64A. The magnitude of the spacing 64B may increase along a length of the fastening tabs 64A running from the first tab part 64 to the second tab part 68. The two fastening tabs 64A have lengths 64C running from the second end of the wound/bandage protector body portion 61B to the second tab part 68 which may run parallel to each other. The outer sides of the two fastening tabs 64A may run parallel to each other and may continue the straight lines formed by the sides of the body portion 61 of the wound/bandage protector 60.

FIGS. 26A to 26C illustrate an exemplary method of using the wound/bandage protector 60. In FIG. 26A, the wound-facing side of the body portion 61 of the wound/bandage protector 60 is placed and held against a limb 683. The body portion 61 is then wrapped around the limb 683 in a direction such that the wound-facing side 683 of the body portion 61 faces the limb 683. Then, as shown in FIG. 26B the first catch fastener 63 is secured to the wound-facing side 681 of the body portion 61. Then, the remainder of the body portion 61 from where the first catch fastener 63 is attached to the body portion 61 in the wrapping direction is rotationally extended and, as shown in FIG. 26C, the final fasteners 67 of the fastening tabs 64A are then fastened to the non-wound facing side of the body portion 61.

Figure 14:
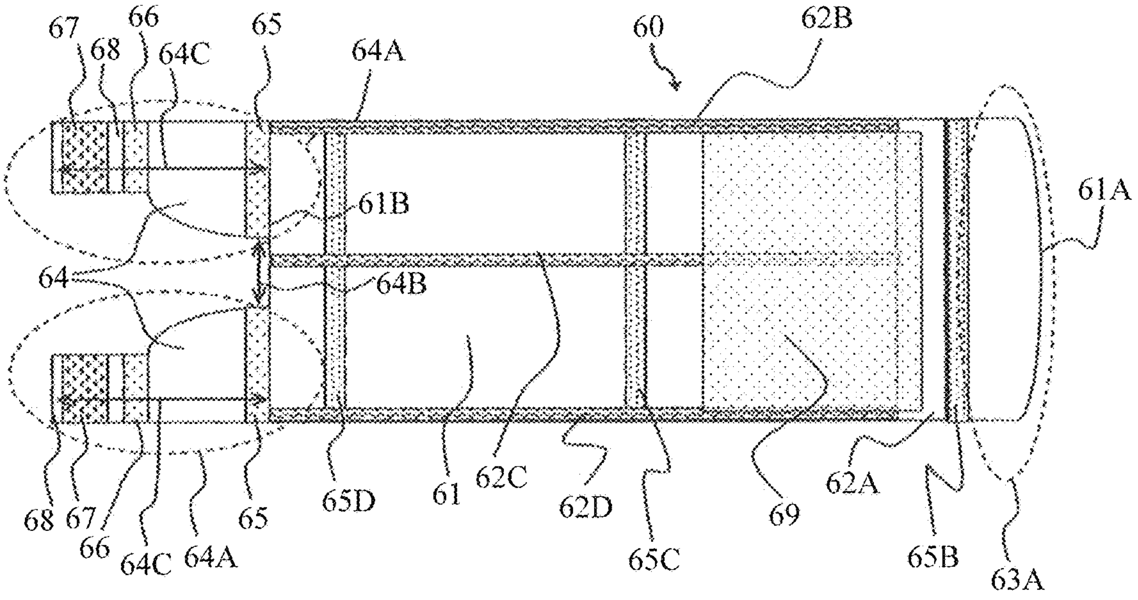
FIG. 14 is an alternative bottom wound facing side view of the exemplary embodiment of the wound/bandage protector illustrated in FIG. 6A.

FIG. 14 shows an alternative exemplary configuration of a bottom view of the wound/bandage protector 60 according to the present invention. In this configuration, instead of the vertical strip 62, there may be a horizontal strip 62B along or proximal to an upper edge of the wound/bandage protector 60, there may be a horizontal strip 62D along or proximal to a lower edge of the wound/bandage protector 60, and there may be a horizontal strip 62C at another position between the strips 62B and 62D of the wound/bandage protector 60. There may also be any combination of these strips, i.e. only strips 62B and 62D, or 62B and 62C, or 62C and 62D, or any one of the strips 62B, 62C or 62D. In an alternative embodiment not shown in the figure, there may be one or more vertical strips along the bottom wound-facing side of wound/bandage 60 rather than horizontal strips. In another alternative embodiment not shown in the figure, rather than vertical or horizontal strips, the entire wound-facing side of the body portion 61 may be provided with a low tack non-slip silicone coating or similar material. According to this exemplary embodiment, there may be a dead zone 65B at or proximal to the first end 61A, there may be a dead zone 65D at or proximal to the second end 61B, and there may be a dead zone 65C preferably at or proximal to the middle of the body portion 61 or at some other position between the dead zone 65B and the dead zone 65D. Alternatively, instead of or in addition to the strips 62B, 62C and 62D, the dead zones 65B, 65C and 65D may be configured as strips as well.

Figure 7A:
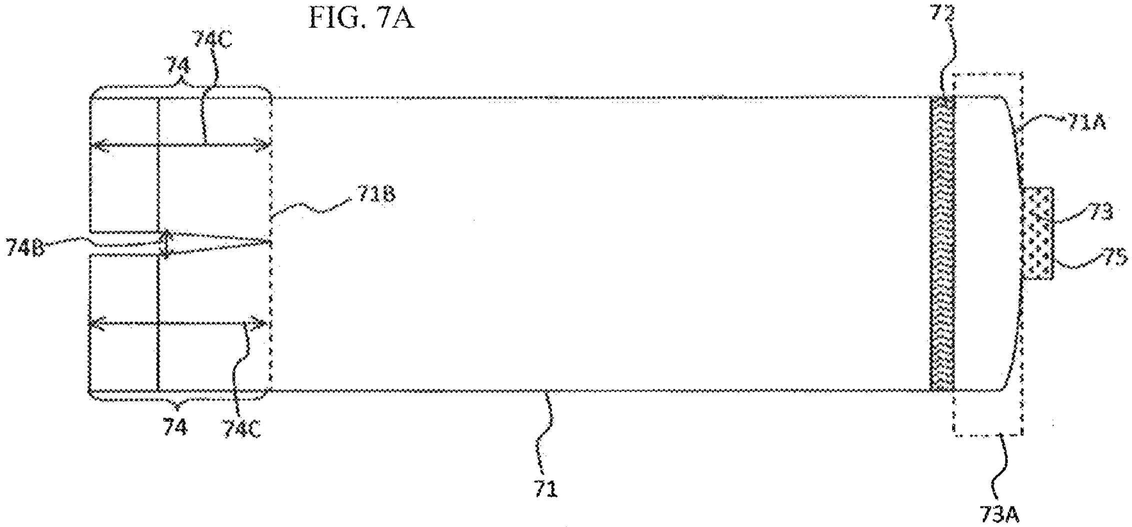
FIG. 7A is a top non-wound facing side view of an exemplary embodiment of a wound/bandage protector according to the present invention.
Figure 7B:
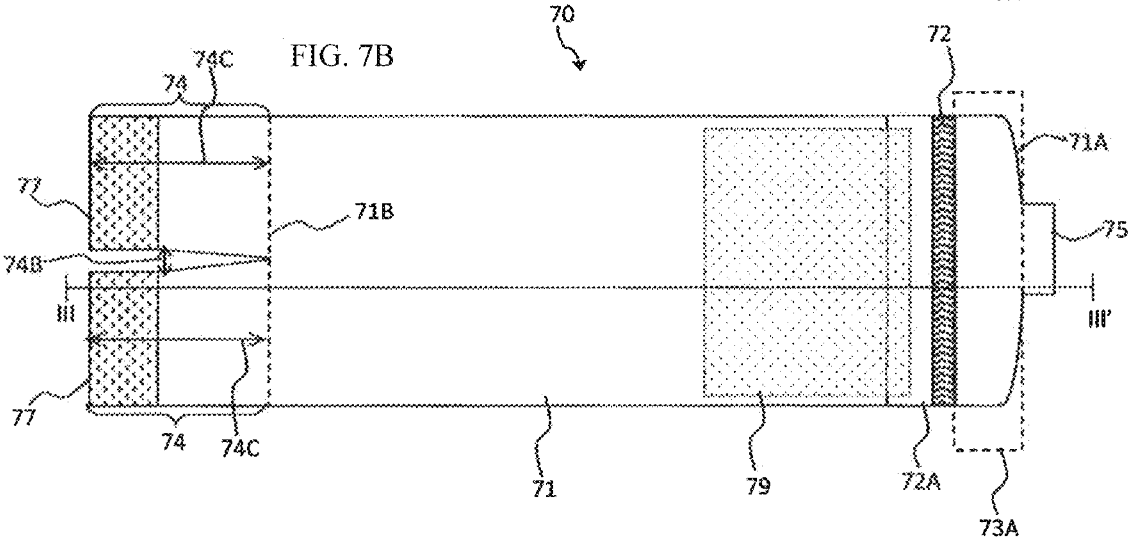
FIG. 7B is a bottom wound facing side view of the exemplary embodiment of the wound/bandage protector illustrated in FIG. 7A.
Figure 7C:
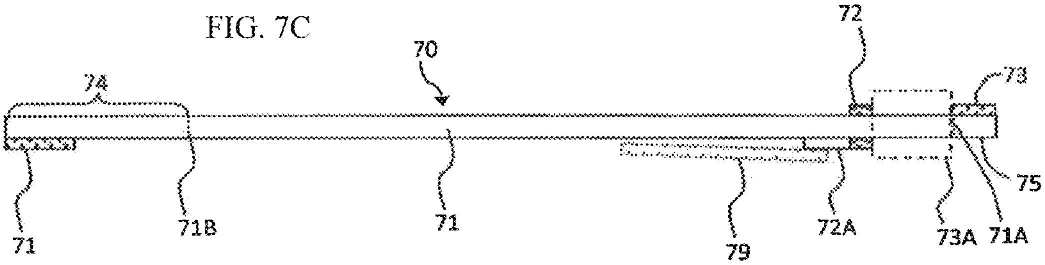
FIG. 7C is a side cross-sectional view of the exemplary embodiment of the wound/bandage protector illustrated in FIGS. 7A and 7B taken along the line III-III' in FIG. 7B.

FIGS. 7A to 7C are, respectively, a top non-wound-facing view, a bottom wound facing view, and a cross-sectional side view taken along the line III-III' of a wound/bandage protector 70 according to the present invention. The exemplary embodiment of the wound/bandage protector 70 has a body portion 71 that is configured as a wrap which may be comprised of super-stretch material similar to the super-stretch material used in the body 21, 31 of the bandage mittens/socks 20, 30. The body portion 71 is configured to act as a loop portion of a Velcro® type fastener on both the bottom wound-facing side of the wound/bandage protector 70 and the top non-wound facing side of the wound/bandage protector 70. The body portion 71 has a length that runs from a first end 71A to a second end 71B. The stretchable material of the body portion 71 at least provides such stretching capacity in a manner that allows the length of the body portion 71 to vary. The stretchable material of the body portion 71 may, alternatively, provide such stretching capacity that allows both the length of the body portion 71 as well as a width of the body portion 71 which is perpendicular to the length of the body portion 71 to vary.

A gauze port 72A is positioned on or integrated into the body portion 71 proximal to the first end 71A of the body portion 71. The gauze port 72A is an area where a gauze pad 79 may be attached or removably attached to the wound-facing side of the body portion 71. The gauze port 72A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, the surface of the gauze port 72A may be comprised of an adhesive that allows for the permanent attachment of the gauze pad 79.

The gauze port 72A may be used to attach different sized gauze pads 79 as well as to periodically replace the gauze pad 79 in the wound/bandage protector 70 shown in this embodiment. The gauze port 72A may be sized and or configured so as to attach to all, a substantial portion, or a small portion such as one side of the gauze pad 79.

In closer proximity to the first end 71A of the body portion 71 of the wound/bandage protector 70 than the gauze port 72A, is a strip 72, which may be similar in configuration to the strip 4 in the first embodiment, having one or more threads made of a rubberized material that provides a moderate amount of friction interwoven in the strip 72 in such a manner that the rubberized material threads are exposed. Alternatively, the strip 72 may be made of other material that provides a frictional surface. Preferably, the amount of friction provided by the frictional surface of the strip 72 should be one that does not cause discomfort when the wound/bandage protector 70 is worn. The strip 72 could be configured so that it is not stretchable in either one or both of the length or the width directions. The strip 72 may be provided along the top non-wound facing side of the wound/bandage protector 70 and/or the bottom wound facing side of the wound/bandage protector 70. Moreover, the strip 72 may extend around sides of the wound/bandage protector 70 and along both the top non-wound facing side of the wound/bandage protector 70 and the bottom wound facing side of the wound/bandage protector 70 so as to form an annular shape.

An end region 73A of the body portion 71 extends from the strip 72 to the first end 71A of the body portion 71. A portion of the end region 73A may be tapered so as to provide a gradual diminution in the width of the body portion 71 toward the first end 71A. A tab 75 extends from the first end 71A of the body portion 71. The tab 75 may be centered along the outer edge of the first end 71A. On the tab 75 is a first-catch fastener 73 on the top non-wound-facing side of the wound/bandage protector 70 that is configured so as to be capable of fastening with the wound facing side of the body portion 71. The first-catch fastener 73 may also extend onto the end region 73A.

FIGS. 27A-27C illustrate an exemplary method of using the wound/bandage protector In FIG. 27A, the wound-facing side of the body portion 71 of the wound/bandage protector 70 is placed and held against a limb 783. The body portion 71 is then wrapped around the limb 783 in a direction such that the wound-facing side 783 of the body portion 71 faces the limb 783. Then, as shown in FIG. 27B the first catch fastener 73 is secured to the wound-facing side 781 of the body portion 71. Then, the remainder of the body portion 71 from where the first catch fastener 73 is attached to the body portion 71 in the wrapping direction is rotationally extended and, as shown in FIG. 27C, the final fastener 77 is then fastened to the non-wound facing side of the body portion 71. It should be noted that in this embodiment, as well as in other embodiments according to the present invention, the first catch fastener may be fastened to a first position on the wound-facing side of the wound/bandage protector that may be on a tab, rather than on the body portion, that is distinct from a location on the tab where a final fastener is located.

On the second end of the body portion 71B are two fastening tabs 74. The two fastening tabs 74 are a continuation of the same piece of super-stretch material as the body portion 71, thus first-catch fastener 73 is also configured so as to be capable of fastening with the wound facing sides of the fastening tabs 74. There may be a spacing 74B between inner sides of the two fastening tabs 74A at the second end of the wound/bandage protector body portion 71B. The shape of the inner sides of the two fastening tabs 74 may be an angled line as shown in FIGS. 5A and 5B, an arc, an arc combined with a straight line, or any other configuration which would allow for a distance between the two inner sides of the two fastening tabs 74. The magnitude of the spacing 74B may increase along a length of the fastening tabs 74. The two fastening tabs 74 have lengths 74C running from the second end of the wound/bandage protector body portion 71B to the second tab part 78 which may run parallel to each other. Outer sides of the two fastening tabs 74A may run parallel to each other and may continue straight lines formed by the sides of the body portion 71 of the wound/bandage protector 70, as shown in FIGS. 5A and 5B. Alternatively, the outer sides of the two fastening tabs 74 may assume a shape that tapers inwardly, toward the inner sides of the fastening tabs 74A, or outwardly, away from the inner sides of the fastening tabs 74A. A final fastener 77 of each of the two fastening tabs 74 has a Velcro® hook type material on the bottom wound-facing side of the wound/bandage protector 70.

Figure 8A:
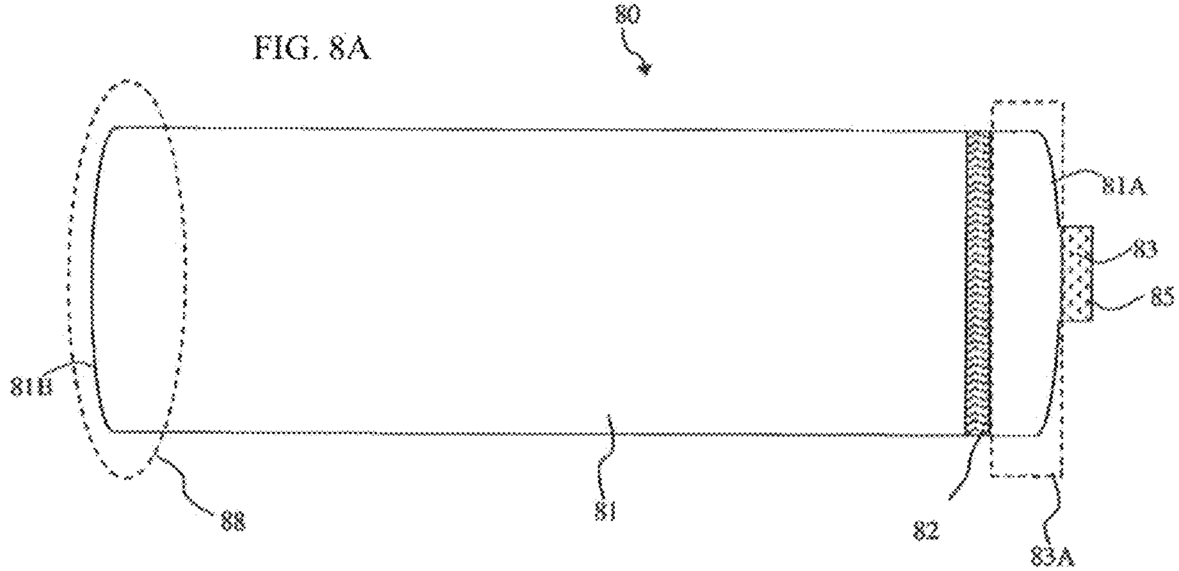
FIG. 8A is a top non-wound facing side view of an exemplary embodiment of a wound/bandage protector according to the present invention.
Figure 8B:
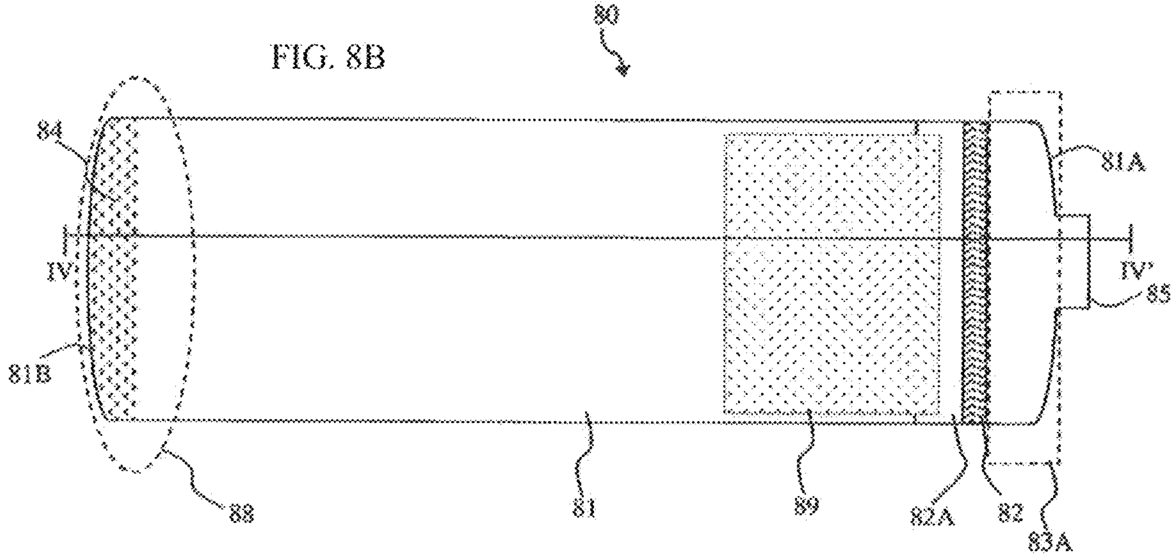
FIG. 8B is a bottom wound facing side view of the exemplary embodiment of the wound/bandage protector illustrated in FIG. 8A.
Figure 8C:
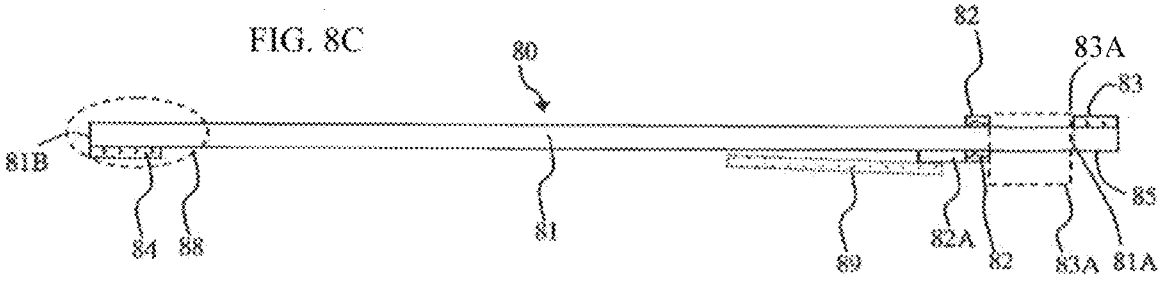
FIG. 8C is a side cross-sectional view of the exemplary embodiment of the wound/bandage protector illustrated in FIGS. 8A and 8B taken along the line IV-IV' in FIG. 8B.

FIGS. 8A to 8C are, respectively, a top non-wound-facing view, a bottom wound facing view, and a cross-sectional side view taken along the line IV-IV' of a wound/bandage protector 80 according to the present invention. The exemplary embodiment of the wound/bandage protector 80 has a body portion 81 that is configured as a wrap which may be comprised of super-stretch material similar to the super-stretch material used in the body 21, 31 of the bandage mittens/socks 20, 30. The body portion 81 is configured to act as a loop portion of a Velcro® type fastener on both the bottom wound-facing side of the wound/bandage protector 80 and the top non-wound facing side of the wound/bandage protector 80. The body portion 81 has a length that runs from a first end 81A to a second end 81B. The stretchable material of the body portion 81 at least provides such stretching capacity in a manner that allows the length of the body portion 81 to vary. The stretchable material of the body portion 81 may, alternatively, provide such stretching capacity that allows both the length of the body portion 81 as well as a width of the body portion 81 which is perpendicular to the length of the body portion 81 to vary.

A gauze port 82A is positioned on or integrated into the body portion 81 proximal to the first end 81A of the body portion 81. The gauze port 82A is an area where a portion of a gauze pad 89 may be attached or removably attached to the wound-facing side of the body portion 81.

The gauze port 82A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, the surface of the gauze port 82A may be comprised of an adhesive that allows for the permanent attachment of the gauze pad 89.

The gauze port 82A may be used to attach different sized gauze pads 89 as well as to periodically replace the gauze pad 89 in the wound/bandage protector 80 shown in this embodiment. The gauze port 82A may be sized and or configured so as to attach to all, a substantial portion, or a small portion such as one side of the gauze pad 89.

In closer proximity to the first end 81A of the body portion 81 of the wound/bandage protector 80 than the gauze port 82A, is a strip 82, which may be similar in configuration to the strip 4 in the first embodiment, having one or more threads made of a rubberized material that provides a moderate amount of friction interwoven in the strip 82 in such a manner that the rubberized material threads are exposed. Alternatively, the strip 82 may be made of other material that provides a frictional surface. Preferably, the amount of friction provided by the frictional surface of the strip 82 should be one that does not cause discomfort when the wound/bandage protector 80 is worn. The strip 82 could be configured so that it is not stretchable in either one or both of the length or the width directions. The strip 82 may be provided along the top non-wound facing side of the wound/bandage protector 80 and/or the bottom wound facing side of the wound/bandage protector 80. Moreover, the strip 82 may extend around sides of the wound/bandage protector 80 and along both the top non-wound facing side of the wound/bandage protector 80 and the bottom wound facing side of the wound/bandage protector 80 so as to form an annular shape.

An end region 83A of the body portion 81 extends from the strip 82 to the first end 81A of the body portion 81. A portion of the end region 83A may be tapered so as to provide a gradual diminution in the width of the body portion 81 toward the first end 81A. A tab 85 extends from the first end 81A of the body portion 81. The tab 85 may be centered along the outer edge of the first end 81A. On the tab 85 is a first-catch fastener 83 on the top non-wound-facing side of the wound/bandage protector 80. The first-catch fastener 83 may also extend onto the end region 83A.

A second end region 88 extends along the body portion 81 from a point along the length of the body portion 81 that is proximal to the second end 81B of the body portion 81, to the second end 81B. A portion of the end region 88 may be tapered so as to provide a gradual diminution in the width of the body portion 81 toward the second end 81B. On the second end region 88, although not necessarily on the entire second end region 88, is a final fastener 84 that can engage and hold fast to the body portion 81 on the top non-wound facing side of the wound/bandage protector 80, or a portion thereof. The final fastener 84 may be made of a Velcro® hook type material provided on the bottom wound-facing side of the wound/bandage protector 80. FIGS. 28A to 28C illustrate an exemplary method of using the wound/bandage protector 80. In FIG. 28A, the wound-facing side of the body portion 81 of the wound/bandage protector 70 is placed and held against a limb 783. The body portion 81 is then wrapped around the limb 783 in a direction such that the wound-facing side 783 of the body portion 81 faces the limb 883. Then, as shown in FIG. 28B the first catch fastener 83 is secured to the wound-facing side 881 of the body portion 71. Then, the remainder of the body portion 71 from where the first catch fastener 73 is attached to the body portion 71 in the wrapping direction is rotationally extended and, as shown in FIG. 28C, the final fastener 84 is then fastened to the non-wound facing side 882 of the body portion 81.

Figure 9A:
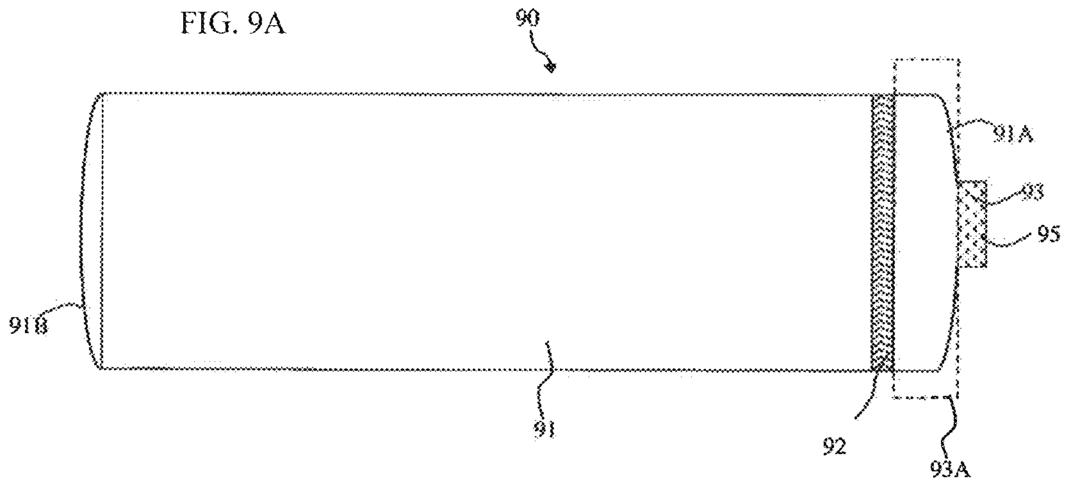
FIG. 9A is a top non-wound facing side view of an exemplary embodiment of a wound/bandage protector according to the present invention.
Figure 9B:
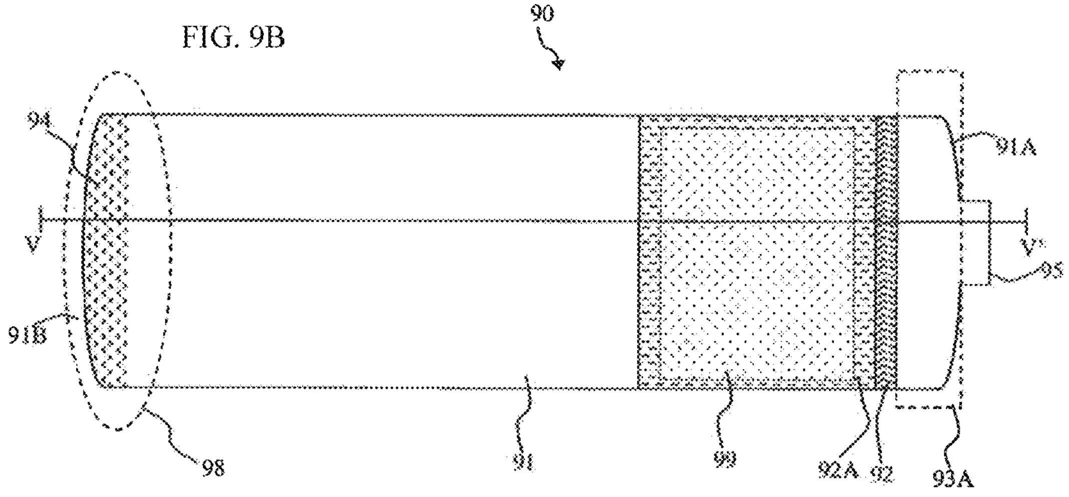
FIG. 9B is a bottom wound facing side view of the exemplary embodiment of the wound/bandage protector illustrated in FIG. 9A.
Figure 9C:
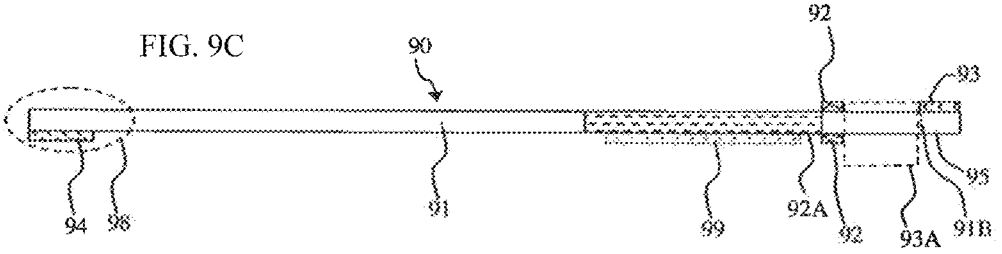
FIG. 9C is a side cross-sectional view of the exemplary embodiment of the wound/bandage protector illustrated in FIGS. 9A and 9B taken along the line V-V' in FIG. 9B.

FIGS. 9A to 9C are, respectively, a top non-wound-facing view, a bottom wound facing view, and a cross-sectional side view taken along the line V-V' of a wound/bandage protector 90 according to the present invention. The exemplary embodiment of the wound/bandage protector 90 has a body portion 91 that is configured as a wrap which may be comprised of super-stretch material similar to the super-stretch material used in the body 21, 31 of the bandage mittens/socks 20, 30. The body portion 91 is configured to act as a loop portion of a Velcro® type fastener on both the bottom wound-facing side of the wound/bandage protector 90 and the top non-wound facing side of the wound/bandage protector 90. The body portion 91 has a length that runs from a first end 91A to a second end 91B. The stretchable material of the body portion 91 at least provides such stretching capacity in a manner that allows the length of the body portion 91 to vary. The stretchable material of the body portion 91 may, alternatively, provide such stretching capacity that allows both the length of the body portion 91 as well as a width of the body portion 91 which is perpendicular to the length of the body portion 91 to vary.

A gauze panel 92A is positioned on or integrated into the body portion 91 proximal to the first end 91A of the body portion 91. The gauze panel 92A is an area where all or substantially all of a gauze pad 99 may be attached or removably attached to the wound-facing side of the body portion 91. The gauze panel 92A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, the surface of the gauze panel 92A may be comprised of an adhesive that allows for the permanent attachment of the gauze pad 99. The gauze panel 92A may be used to attach different sized gauze pads 99 as well as to periodically replace the gauze pad 99 in the wound/bandage protector 90 shown in this embodiment.

In closer proximity to the first end 91A of the body portion 91 of the wound/bandage protector 90 than the gauze panel 92A, may be a strip 92, which may be similar in configuration to the strip 4 in the first embodiment, having one or more threads made of a rubberized material that provides a moderate amount of friction interwoven in the strip 92 in such a manner that the rubberized material threads are exposed. Alternatively, the strip 92 may be made of other material that provides a frictional surface. Preferably, the amount of friction provided by the frictional surface of the strip 92 should be one that does not cause discomfort when the wound/bandage protector 90 is worn. The strip 92 could be configured so that it is not stretchable in either one or both of the length or the width directions. The strip 92 may be provided along the top non-wound facing side of the wound/ bandage protector 90 and/or the bottom wound facing side of the wound/bandage protector 90. Moreover, the strip 92 may extend around sides of the wound/bandage protector 90 and along both the top non-wound facing side of the wound/bandage protector 90 and the bottom wound facing side of the wound/bandage protector 90 so as to form an annular shape.

An end region 93A of the body portion 91 extends from the strip 92 to the first end 91A of the body portion 91. A portion of the end region 93A may be tapered so as to provide a gradual diminution in the width of the body portion 91 toward the first end 91A. A tab 95 extends from the first end 91A of the body portion 91. The tab 95 may be centered along the outer edge of the first end 91A. On the tab 95 is a first-catch fastener 93 on the top non-wound-facing side of the wound/bandage protector 90. The first-catch fastener 93 may also extend onto the end region 93A.

A second end region 98 extends along the body portion 91 from a point along the length of the body portion 91 that is proximal to the second end 91B of the body portion 91, to the second end 91B. A portion of the end region 98 may be tapered so as to provide a gradual diminution in the width of the body portion 91 toward the second end 91B. On the second end region 98, although not necessarily on the entire second end region 98, is a final fastener 94 that can engage and hold fast to the body portion 91 on the top non-wound facing side of the wound/bandage protector 90, or a portion thereof. The final fastener 94 may be made of a Velcro® hook type material provided on the bottom wound-facing side of the wound/bandage protector 90.

Figure 10A:
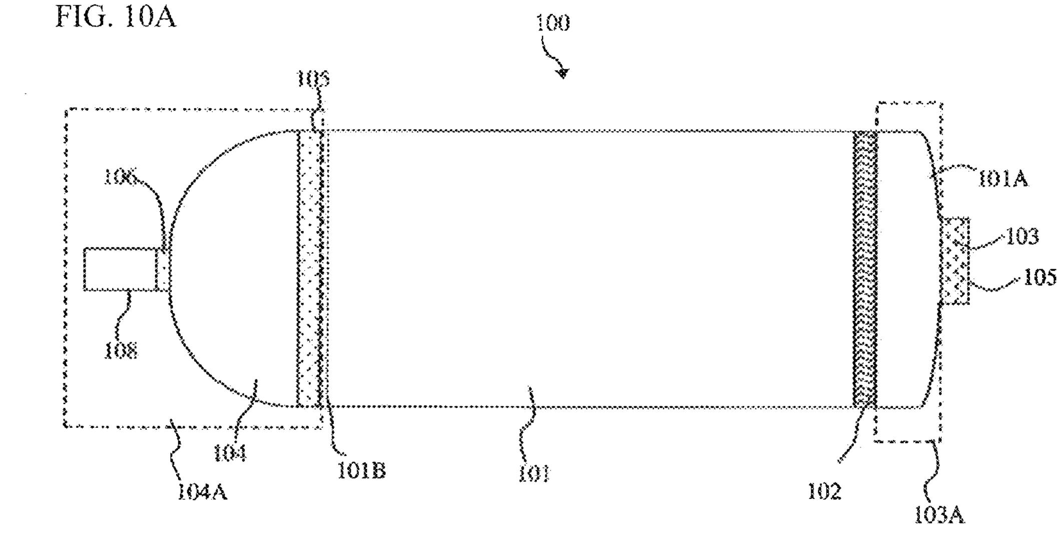
FIG. 10A is a top non-wound facing side view of an exemplary embodiment of a wound/bandage protector according to the present invention.
Figure 10B:
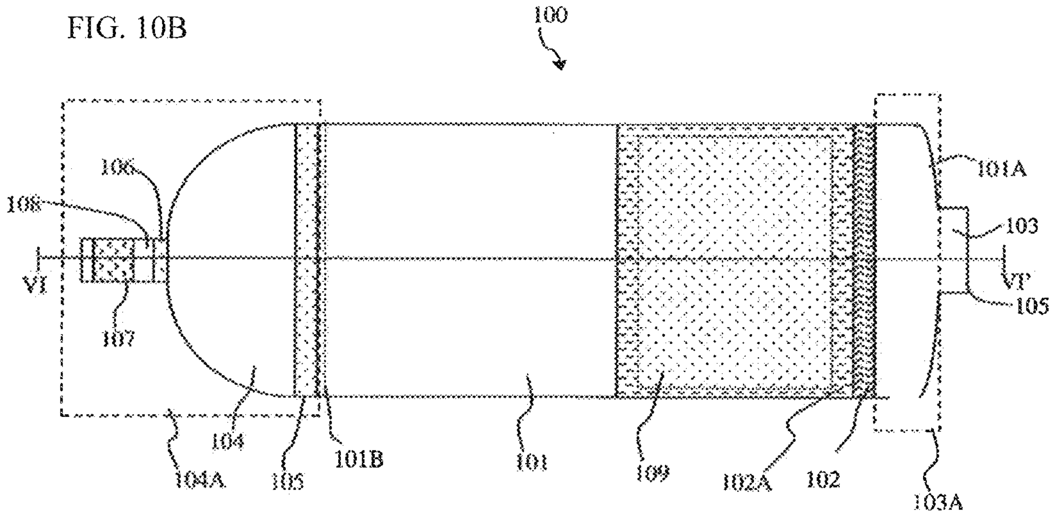
FIG. 10B is a bottom wound facing side view of the exemplary embodiment of the wound/bandage protector illustrated in FIG. 10A.
Figure 10C:
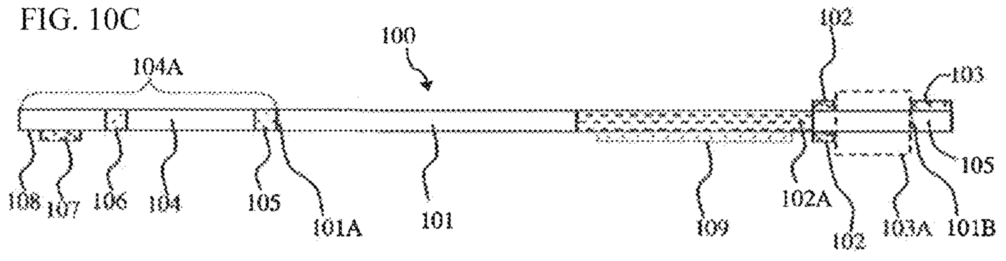
FIG. 10C is a side cross-sectional view of the exemplary embodiment of the wound/bandage protector illustrated in FIGS. 10A and 10B taken along the line VI-VI' in FIG. 10B.

FIGS. 10A to 10C are, respectively, a top non-wound-facing view, a bottom wound facing view, and a cross-sectional side view taken along the line VI-VI' of a wound/bandage protector 100 according to the present invention. The exemplary embodiment of the wound/bandage protector 100 has a body portion 101 that is configured as a wrap, which may be comprised of super-stretch material similar to the super-stretch material used in the body 21, 31 of the bandage mittens/socks 20, 30. The body portion 101 is configured to act as a loop portion of a Velcro® type fastener on both the bottom wound-facing side of the wound/bandage protector 100 and the top non-wound facing side of the wound/bandage protector 100. The body portion 101 has a length that runs from a first end 101A to a second end 101B. The stretchable material of the body portion 101 at least provides such stretching capacity in a manner that allows the length of the body portion 101 to vary. The stretchable material of the body portion 101 may, alternatively, provide such stretching capacity that allows both the length of the body portion 101 as well as a width of the body portion 101 which is perpendicular to the length of the body portion 101 to vary.

A gauze panel 102A is positioned on or integrated into the body portion 101 proximal to the first end 101A of the body portion 101. The gauze panel 102A is an area where all or substantially all of a gauze pad 109 may be attached or removably attached to the wound-facing side of the body portion 101. The gauze panel 102A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, the surface of the gauze panel 102A may be comprised of an adhesive that allows for the permanent attachment of the gauze pad 109. The gauze panel 102A may be used to attach different sized gauze pads 109 as well as to periodically replace the gauze pad 109 in the wound/bandage protector 100 shown in this embodiment.

In closer proximity to the first end 101A of the body portion 101 of the wound/bandage protector 100 than the gauze panel 102A, may be a strip 102, which may be similar in configuration to the strip 4 in the first embodiment, having one or more threads made of a rubberized material that provides a moderate amount of friction interwoven in the strip 102 in such a manner that the rubberized material threads are exposed. Alternatively, the strip 102 may be made of other material that provides a frictional surface. Preferably, the amount of friction provided by the frictional surface of the strip 102 should be one that does not cause discomfort when the wound/bandage protector 100 is worn. The strip 102 could be configured so that it is not stretchable in either one or both of the length or the width directions. The strip 102 may be provided along the top non-wound facing side of the wound/bandage protector 100 and/or the bottom wound facing side of the wound/bandage protector 100. Moreover, the strip 102 may extend around sides of the wound/bandage protector 100 and along both the top non-wound facing side of the wound/bandage protector 100 and the bottom wound facing side of the wound/bandage protector 100 so as to form an annular shape.

An end region 103A of the body portion 101 extends from the strip 102 to the first end 101A of the body portion 101. A portion of the end region 103A may be tapered so as to provide a gradual diminution in the width of the body portion 101 toward the first end 101A. A tab 105 extends from the first end 101A of the body portion 101. The tab 105 may be centered along the outer edge of the first end 101A. On the tab 105 is a first-catch fastener 103 on the top non-wound-facing side of the wound/bandage protector 100. The first-catch fastener 103 may also extend onto the end region 103A.

Attached to the second end of the body portion 101B is a fastening tab 104A. The fastening tab 104A may be comprised of two parts. A first tab part 104 is attached to the second end of the wound/bandage protector body portion 101B and is made out of a super-stretch material which may be adapted to function as a loop portion of a Velcro®-type fastener on both the top non-wound facing side and the bottom wound-facing side of the wound/bandage protector 100. The super-stretch material of the first tab part 104 preferably provides a stretching resistance that is greater than the stretching resistance of the body portion 101. The first tab part 104 may be attached to the second end of the wound/bandage protector body portion 101B via an attachment region 105 which is preferably configured to provide no stretch. The attachment region 105 may be comprised of a composite of the material of the first tab part 104 and the body portion 101 of the wound/bandage protector 100 and may be attached by a punch and melt heat seal. Alternatively, the first tab part 104 is directly attached to the body portion 101 without an attachment region 105 intervening therebetween. A second tab part 108 is attached to the first tab part 104 via an attachment region 106. The attachment region 106 may be comprised of a composite of the material of the first tab part 104 and the second tab part 108 and may be attached by a punch and melt heat seal. The second tab part 108 has a portion 107 which includes a Velcro® hook type material on the bottom wound-facing side of the fastening tab 104A. Alternatively, the second tab part 108 is directly attached to the first tab part 104 without an attachment region 106 intervening therebetween.

Figure 11A:
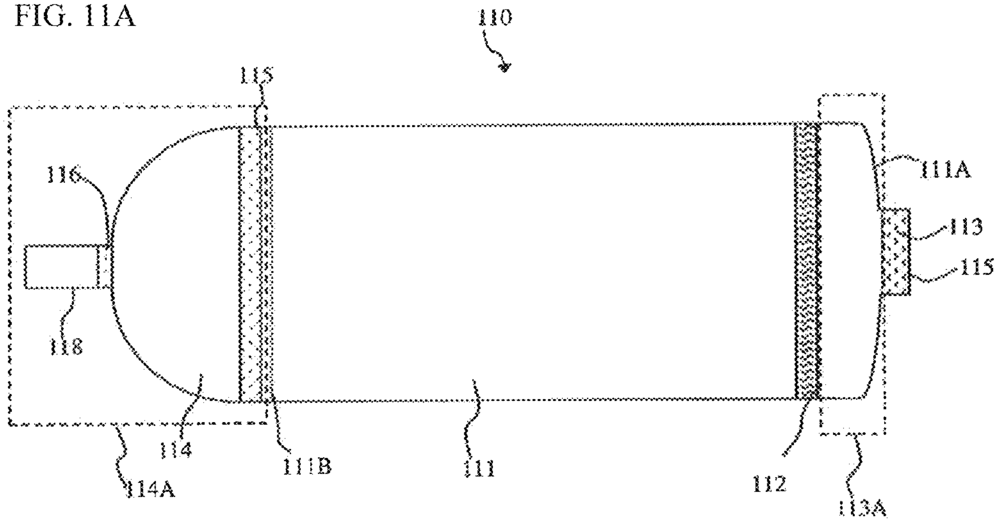
FIG. 11A is a top non-wound facing side view of an exemplary embodiment of a wound/bandage protector according to the present invention.
Figure 11B:
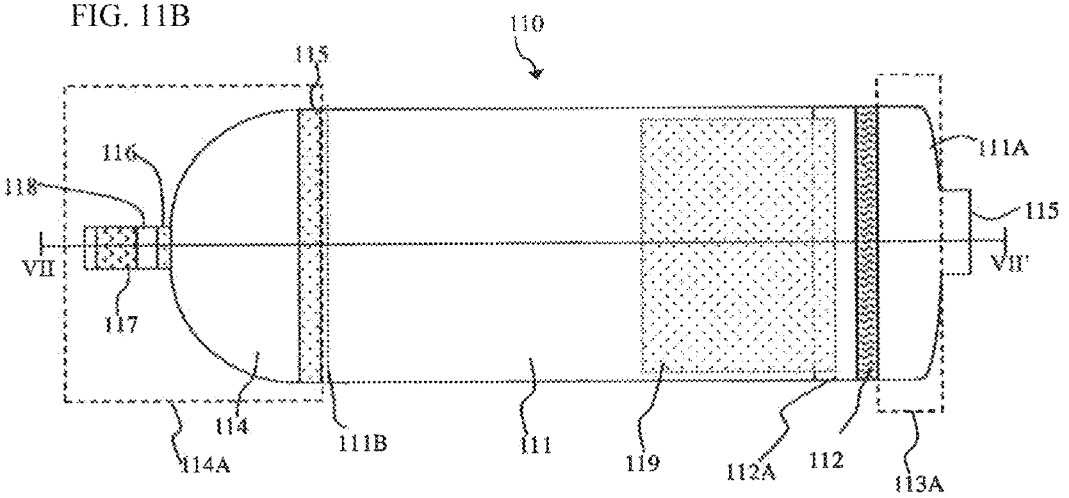
FIG. 11B is a bottom wound facing side view of the exemplary embodiment of the wound/bandage protector illustrated in FIG. 11A.
Figure 11C:
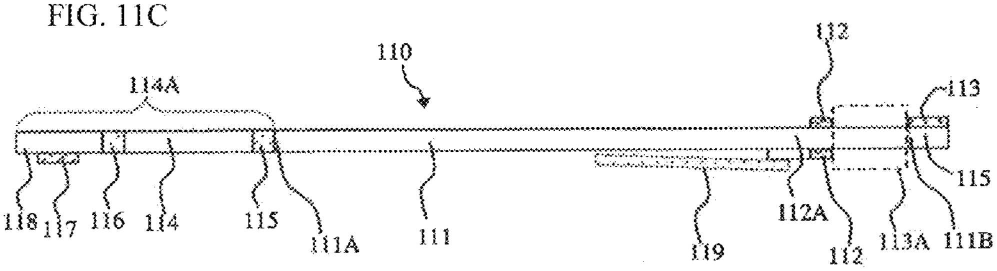
FIG. 11C is a side cross-sectional view of the exemplary embodiment of the wound/bandage protector illustrated in FIGS. 11A and 11B taken along the line VII-VII' in FIG. 11B.

FIGS. 11A to 11C are, respectively, a top non-wound-facing view, a bottom wound facing view, and a cross-sectional side view taken along the line VII-VII' of a wound/bandage protector 110 according to the present invention. The exemplary embodiment of the wound/bandage protector 110 has a body portion 111 that is configured as a wrap, which may be comprised of super-stretch material similar to the super-stretch material used in the body 21, 31 of the bandage mittens/socks 20, 30. The body portion 111 is configured to act as a loop portion of a Velcro® type fastener on both the bottom wound-facing side of the wound/bandage protector 110 and the top non-wound facing side of the wound/bandage protector 110. The body portion 111 has a length that runs from a first end 111A to a second end 111B. The stretchable material of the body portion 111 at least provides such stretching capacity in a manner that allows the length of the body portion 111 to vary. The stretchable material of the body portion 111 may, alternatively, provide such stretching capacity that allows both the length of the body portion 111 as well as a width of the body portion 111 which is perpendicular to the length of the body portion 111 to vary.

A gauze port 112A is attached to the body portion 111 proximal to the first end 111A of the body portion 111. The gauze port 112A is an area where a portion of a gauze pad 119 may be attached or removably attached to the wound-facing side of the body portion 111. The gauze port 112A may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, the surface of the gauze port 112A may be comprised of an adhesive that allows for the permanent attachment of the gauze pad 119. The gauze port 112A may be used to attach different sized gauze pads 119 as well as to periodically replace the gauze pad 119 in the wound/bandage protector 110 shown in this embodiment. The gauze port 112A may be sized and or configured so as to attach to all, a substantial portion, or a small portion such as one side of the gauze pad 119.

In closer proximity to the first end 111A of the body portion 111 of the wound/bandage protector 110 than the gauze port 112A, may be a strip 112, which may be similar in configuration to the strip 4 in the first embodiment, having one or more threads made of a rubberized material that provides a moderate amount of friction interwoven in the strip 112 in such a manner that the rubberized material threads are exposed. Alternatively, the strip 112 may be made of other material that provides a frictional surface. Preferably, the amount of friction provided by the frictional surface of the strip 112 should be one that does not cause discomfort when the wound/bandage protector 110 is worn. The strip 112 could be configured so that it is not stretchable in either one or both of the length or the width directions. The strip 112 may be provided along the top non-wound facing side of the wound/bandage protector 110 and/or the bottom wound facing side of the wound/bandage protector 110. Moreover, the strip 112 may extend around sides of the wound/bandage protector 110 and along both the top non-wound facing side of the wound/bandage protector 110 and the bottom wound facing side of the wound/bandage protector 110 so as to form an annular shape.

An end region 113A of the body portion 111 extends from the strip 112 to the first end 111A of the body portion 111. A portion of the end region 113A may be tapered so as to provide a gradual diminution in the width of the body portion 111 toward the first end 111A. A tab 115 extends from the first end 111A of the body portion 111. The tab 115 may be centered along the outer edge of the first end 111A. On the tab 115 is a first-catch fastener 113 on the top non-wound-facing side of the wound/bandage protector 110. The first-catch fastener 113 may also extend onto the end region 113A.

Figure 12A:
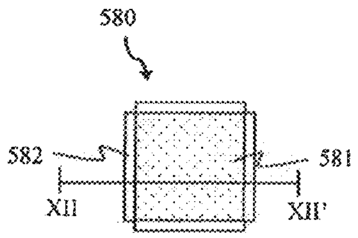
FIG. 12A is a top view of an exemplary embodiment of a frictional gauze pad according to the present invention.
Figure 12B:
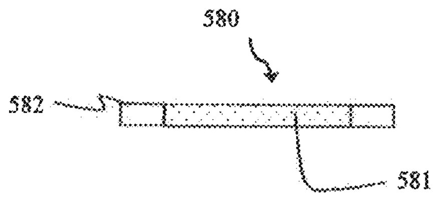
FIG. 12B is a side cross-sectional view of the frictional gauze pad illustrated in FIG. 12A taken along line XII-XII'.

Attached to the second end of the body portion 111B is a fastening tab 114A. The fastening tab 114A may be comprised of two parts. A first tab part 114 is attached to the second end of the wound/bandage protector body portion 111B and is made out of a super-stretch material which may be adapted to function as a loop portion of a Velcro®-type fastener on both the top non-wound facing side and the bottom wound-facing side of the wound/bandage protector 110. The super-stretch material of the first tab part 114 preferably provides a stretching resistance that is greater than the stretching resistance of the body portion 111. The first tab part 114 may be attached to the second end of the wound/bandage protector body portion 111B via an attachment region 115 which is preferably configured to provide no stretch. The attachment region 115 may be comprised of a composite of the material of the first tab part 114 and the body portion 111 of the wound/bandage protector 110 and may be attached by a punch and melt heat seal. Alternatively, the first tab part 114 is directly attached to the body portion 111 without an attachment region 115 intervening therebetween. A second tab part 118 is attached to the first tab part 114 via an attachment region 116. The attachment region 116 may be comprised of a composite of the material of the first tab part 114 and the second tab part 118 and may be attached by a punch and melt heat seal. The second tab part 118 has a portion 117 which includes a Velcro® hook type material on the bottom wound-facing side of the fastening tab 114A. Alternatively, the second tab part 118 is directly attached to the first tab part 114 without an attachment region 116 intervening therebetween. FIGS. 12A and 12B are, respectively, a top view and a side cross-sectional view taken along line XII-XII' of an exemplary embodiment of a frictional gauze pad 580 according to the present invention. The frictional gauze pad 580 has a pad portion 581 and a frame 582. The pad portion 581 may be comprised of materials similar to that of the frictional gauze pads discussed above. The frame 582 is attached to and extends from the edge of the pad portion 581. The frame 582 may be comprised of a self-adherent material or a rubberized or tacky material and may have a similar configuration as the strip 62 in FIG. 6A above. The frictional gauze pad 580 can be used instead of a gauze port or similar method of securing the gauze in place by providing a frictional or similar resistance between the frame 582 of the frictional gauze pad 580 and a bandage and/or a frictional or similar resistance between the frictional gauze pad 580 and the area surrounding the wound. Thus, for example, in the wound/bandage protector 60, in lieu of providing a gauze port 62A, one may use the frictional gauze pad 580. In addition, the wound/bandage protector 60 may be further configured to include a corresponding self-adherent material or a rubberized or tacky surface on the wound facing side of the body portion 61 to further enhance the frictional or similar resistance between the wound/bandage protector 60 and the frictional gauze pad 580. One skilled in the art would understand that this frictional gauze pad 580 may be applied to any and all of the bandages discussed above as well as to other bandages known in the art.

Figure 13A:
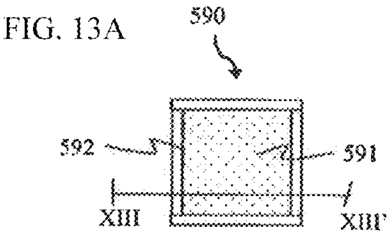
FIG. 13A is a top view of an exemplary embodiment of a frictional gauze pad according to the present invention.

FIGS. 13A to 13E show alternative exemplary embodiments of a frictional gauze pad according to the present invention. FIG. 13A may be a top view and/or a bottom view of a gauze pad 590 with a pad portion 591 and a frame 592.

Figure 13B:
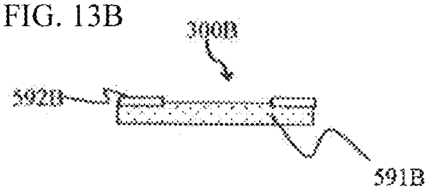
FIG. 13B is a first exemplary cross-sectional view of the frictional gauze pad illustrated in FIG. 13A taken along line XIII-XIII'.
Figure 13C:
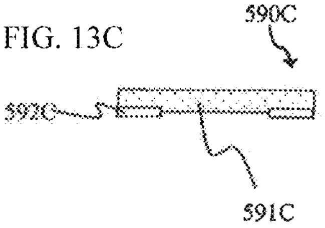
FIG. 13C is a second exemplary cross-sectional view of the frictional gauze pad illustrated in FIG. 13A taken along line XIII-XIII'.
Figure 13D:
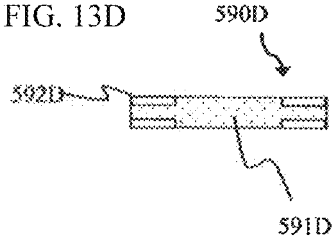
FIG. 13D is a third exemplary cross-sectional view of the frictional gauze pad illustrated in FIG. 13A taken along line XIII-XIII'.
Figure 13E:
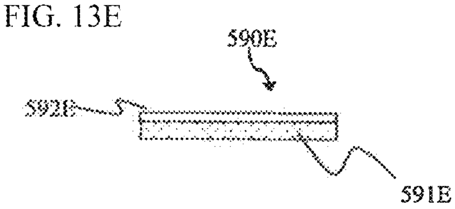
FIG. 13E is an alternative exemplary cross-sectional view of the frictional gauze pad according to the present invention.

The pad portion 591 may be comprised of materials similar to that of the frictional gauze pad 290, discussed above. The frame 592 may be affixed to the top and/or bottom surface of the pad portion 591. Alternatively, the frame 592 may be attached to and extend from the edge of the pad portion 591. The frame 592 may be comprised of a self-adherent material or a rubberized or tacky material. FIG. 13B is a side cross-sectional view of one alternative embodiment of a frictional gauze pad 590B, with a frame 592B, that has the same configuration as the frame 592, attached to the top surface of a pad portion 591B of the frictional gauze pad 590B. FIG. 13C is a side cross-sectional view of another alternative embodiment of a frictional gauze pad 590C, with a frame 592C, that has the same configuration as the frame 592, attached to the bottom surface of a pad portion 591C of the frictional gauze pad 590C. FIG. 13D is a side cross-sectional view of another alternative embodiment of a frictional gauze pad 590D, with a frame 592D, that has the same configuration as the frame 592, attached to both the top surface and the bottom surface of a pad portion 591D of the frictional gauze pad 590D. FIG. 13E is a side cross-sectional view of another alternative embodiment of a frictional gauze pad 590E in which a frame 592E is extended to cover the entire top surface of a pad portion 591E. This embodiment may be combined with the frictional gauze pad 590C in which the frame 592C is attached to the bottom of the pad portion 591C.

Figure 18A:
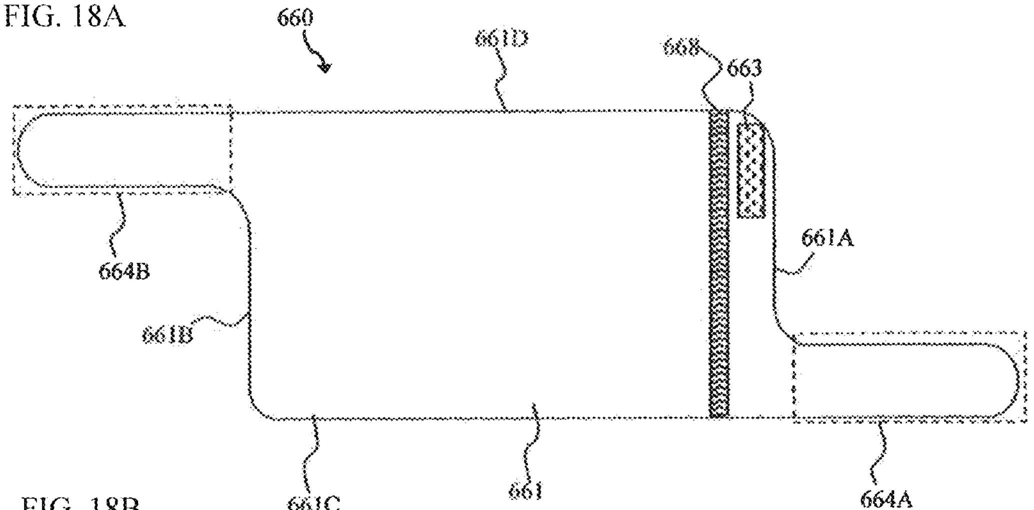
FIG. 18A is a top non-wound facing side view of an exemplary embodiment of a wound/bandage protector according to the present invention.
Figure 18B:
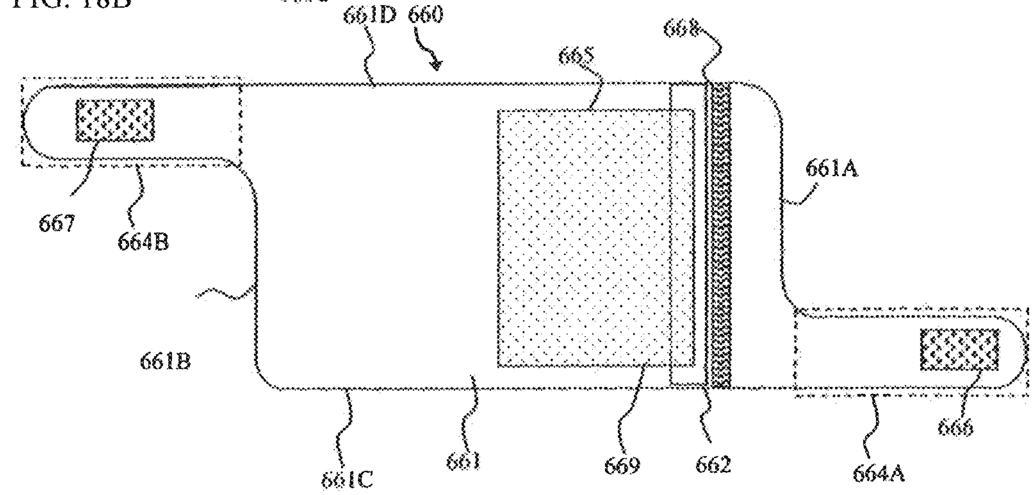
FIG. 18B is a bottom wound facing side view of the exemplary embodiment of the wound/bandage protector illustrated in FIG. 18A.
Figure 18C:
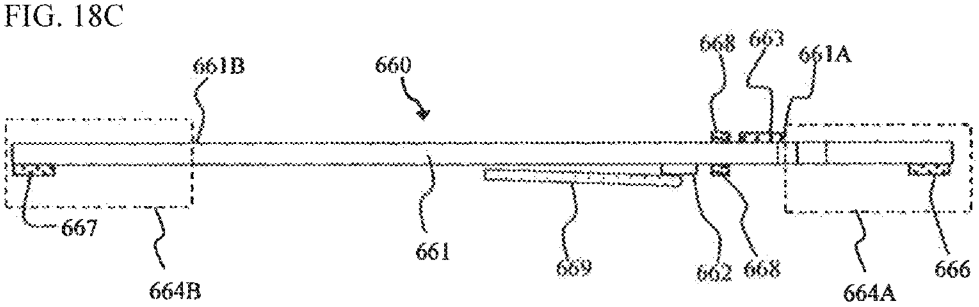
FIG. 18C is a side view of the exemplary embodiment of the wound/bandage protector illustrated in FIGS. 18A and 18B.

FIGS. 18A to 18C are, respectively, a top non-wound-facing view, a bottom wound facing view, and a side view of a wound/bandage protector 660 according to the present invention. The exemplary embodiment of the wound/bandage protector 660 has a body portion 661 that is configured as a wrap which may be comprised of super-stretch material similar to the super-stretch material used in the body 21, 31 of the bandage mittens/socks 20, 30. The body portion 661 is configured to act as a loop portion of a Velcro® type fastener on both the bottom wound-facing side of the wound/bandage protector 660 and the top non-wound facing side of the wound/bandage protector 660. The body portion 661 has a length that runs from a first end 661A to a second end 661B. The stretchable material of the body portion 661 at least provides such stretching capacity in a manner that allows the length of the body portion 661 to vary. The stretchable material of the body portion 661 may, alternatively, provide such stretching capacity that allows both the length of the body portion 661 as well as a width of the body portion 661 which is perpendicular to the length of the body portion 661 to vary.

A gauze port 662 is positioned on or integrated into the body portion 661 proximal to the first end of the body portion 661A. The gauze port 662A is an area where a gauze pad 669 may be attached or removably attached to the wound-facing side of the body portion 661. The gauze port 662 may be comprised of non-stretchable material and may have a surface that is configured for repeated removal and attachment of gauze by having either a hook or loop Velcro® type fastening surface or a surface that provides a good bond with a re-stickable adhesive such as that found in Post-It® notes. Alternatively, both the gauze port 662 and the gauze pad 669 may have a low tack adhesive, such as a low tack silicone adhesive. The low tack adhesive may be on the entire non-wound facing side of the gauze pad 669, or may be just on a portion of the non-wound facing side of the gauze pad 669. Another possibility is that the surface of the gauze port 662 may be comprised of an adhesive that allows for the permanent attachment of the gauze pad 669. The gauze port 662 may be used to attach different sized gauze pads 669 as well as to periodically replace the gauze pad 669 in the wound/bandage protector 660 shown in this embodiment. The gauze port 662 may be sized and/or configured so as to attach to all, a substantial portion, or a small portion as illustrated in the FIGS. 18B and 18C, such as one side of the gauze pad 669.

In closer proximity to the first end 661A of the body portion 661 of the wound/bandage protector 660 than the gauze port 662A, is a strip 668, which may be similar in configuration to the strip 4 in the first embodiment, having one or more threads made of a rubberized material that provides a moderate amount of friction interwoven in the strip 668 in such a manner that the rubberized material threads are exposed. Alternatively, the strip 668 may be made of stretch non-slip silicone or similar, preferably latex free, material that provides a frictional surface. The non-slip silicone may be applied in a continuous or discontinuous manner to form the strip 668. Preferably, the amount of friction provided by the frictional surface of the strip 668 should be one that does not cause discomfort when the wound/bandage protector 660 is worn. The strip 668 could be configured so that it is not stretchable in either one or both of the length or the width directions. The strip 668 may be provided along the top non-wound facing side of the wound/bandage protector 660 and/or the bottom wound facing side of the wound/bandage protector 660. Moreover, the strip 668 may extend around sides of the wound/bandage protector 660 and along both the top non-wound facing side of the wound/bandage protector 660 and the bottom wound facing side of the wound/bandage protector 660 so as to form an annular shape.

A first tab 664A extends from the first end 661A of the body portion 661 along, or proximal and substantially with, a line tangential to a lower side 661C of the body portion 661. On the wound facing side of the first tab 664A is a first-attachment region 666 that preferably extends to or proximal to an end of the first tab 664A that is distal to the body portion 661. The first-attachment region 666 is capable of fastening to a portion of the non-wound facing side of the body portion 661. A second tab 664B extends from the second end 661A of the body portion 661 along, or proximal and substantially with, a line tangential to an upper side 661D of the body portion 661. On the wound facing side of the second tab 664A is a second-attachment region 667 that preferably extends to or proximal to an end of the second tab 664B that is distal to the body portion 661. The second-attachment region 666 is capable of fastening to a portion of the non-wound facing side of the body portion 661. In the wound/bandage protector 660 the first and second tabs 664A, 664B are made of the same integral piece of material as the body portion. However, in other alternative embodiments the first and second tabs 664A, 664B may be constructed in the manner described herein by tabs in other exemplary embodiments of the wound bandage protector. The first-attachment region 666 and second attachment region 667 are preferably a hook portion of a Velcro®-type fastener, while the non-wound facing side of the body portion 661 preferably acts as a loop portion of a Velcro®-type fastener. On the top non-wound-facing side of the wound/bandage protector 660 proximal or adjacent to the first end 661A of the body portion is a first-catch fastener 663. The first-catch fastener 663 extends between the upper side 661D and the lower side 661C at least along a portion that is opposing the second tab 664B, such that when the wound/bandage protector 660 is wrapped around a limb a portion of the wound facing side of the second tab 664B may fasten to the first-catch fastener 663. The first-catch fastener

663 is preferably a hook portion of a Velcro®-type fastener, while the wound facing side of the second tab 664B preferably acts as a loop portion of a Velcro®-type fastener.

Figure 15A:
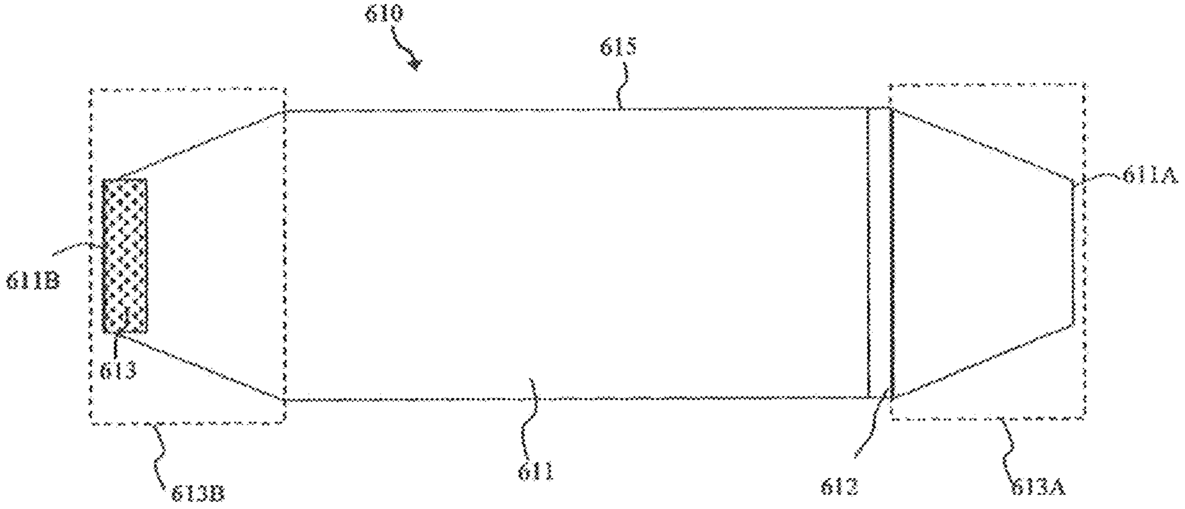
FIG. 15A is a top non-wound facing side view of an exemplary embodiment of a wound/bandage protector according to the present invention.
Figure 15B:
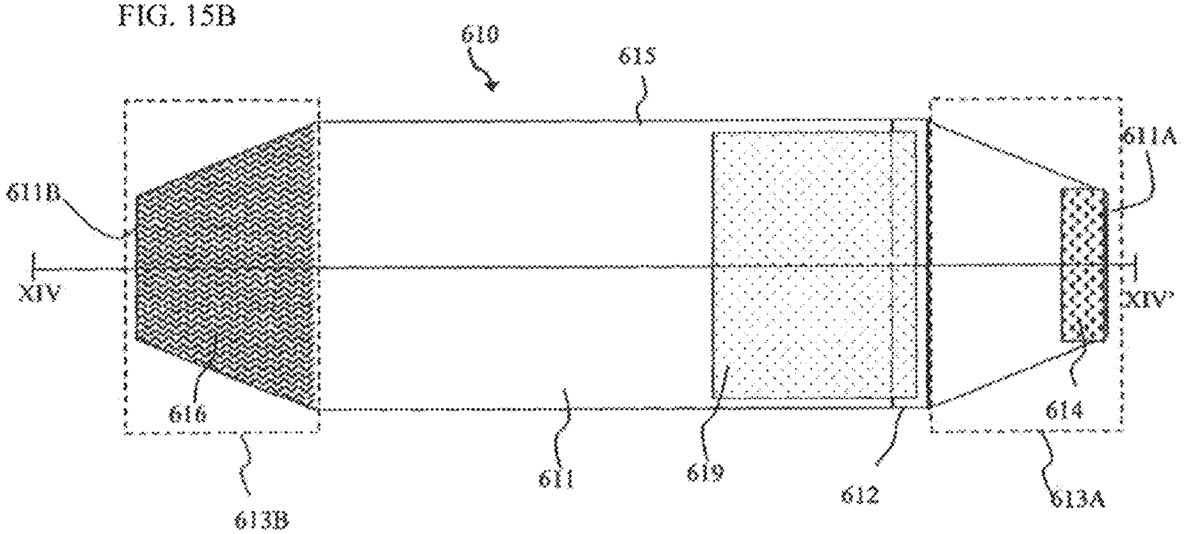
FIG. 15B is a bottom wound facing side view of the exemplary embodiment of the wound/bandage protector illustrated in FIG. 15A.
Figure 15C:
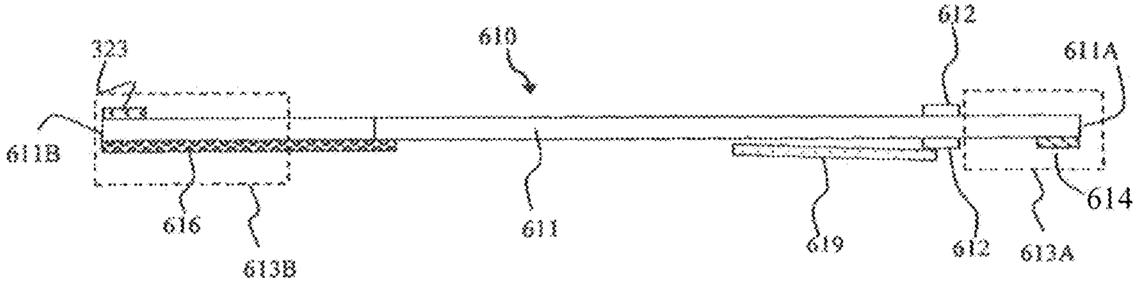
FIG. 15C is a side cross-sectional view of the exemplary embodiment of the wound/bandage protector illustrated in FIGS. 15A and 15B taken along the line XIV-XIV' in FIG. 15B.

FIGS. 15A to 15C are, respectively, a top non-wound facing view, a bottom wound facing view, and a cross-sectional side view taken along the line XIV-XIV' of an exemplary embodiment of a wound/bandage protector 610 according to the present invention. The exemplary embodiment of the wound/bandage protector 610 has a body portion 611 that is configured as a wrap which may be comprised of super-stretch material similar to the super-stretch material used in the body 21, 31 of the bandage mittens/socks 20, 30. The body portion 611 is configured to act as a loop portion of a Velcro® type fastener on both the bottom wound-facing side of the wound/bandage protector 610 and the top non-wound facing side of the wound/bandage protector 610. The body portion 611 has a length that runs from a first end 611A to a second end 611B with a first end region 613A that extends along the length of the body portion 611 from the first end 611A to a central region 615, the central region extending along the length of the body portion from the first end region 613A to a second end region 613B, and the second end region extending along the length of the body portion from the central region 615 to the second end 611B. The stretchable material of the body portion 611 at least provides such stretching capacity in a manner that allows the length of the body portion 611, i.e. the distance between the first end 611A and the second end 611B, to vary. The stretchable material of the body portion 611 may alternatively provide such stretching capacity that allows both the length of the body portion 611 as well as a width of the body portion 611, which is perpendicular to the length of the body portion 611, to vary.

A gauze port 612 is preferably positioned on or integrated into the central region 615 of the body portion 611 adjacent or proximal to the first end region 613A. The gauze port 612 is an area where a portion of a gauze pad 619 may be attached or removably attached to the wound-facing side of the body portion 611. The gauze port 612 may be comprised of non-stretchable material and may have a surface at least on the wound facing side of the wound/bandage protector 610 that is configured for repeated removal and attachment of gauze by having either a hook or loop Velcro® type fastening surface or that provides a good bond with a re-stickable adhesive such as that found in Post-It® notes. Alternatively, the surface of the gauze port 612 at least on the wound facing side of the wound/bandage protector 610 may be configured for permanent attachment of the gauze pad 619 to the body portion such as by permanent adhesive. The gauze port 612 may be used to attach different sized gauze pads 619 as well as to periodically replace the gauze pad 619 in the wound/bandage protector 610 shown in this embodiment. The gauze port 612 may be sized and/or configured so as to attach to all, a substantial portion, or a small portion such as one side of the gauze pad 619.

The first end region 613A is tapered so as to provide a gradual diminution in the width of the body portion 611 as the first end region extends in a length direction toward the first end 611A. On the first end region 613A, although not necessarily on the entire first end region 613A, is a final fastener 614 that can engage and hold fast to the body portion 611 on the top non-wound facing side of the wound/bandage protector 610, or a portion thereof. The final fastener 614 may be made of a Velcro® hook type material provided on the bottom wound-facing side of the wound/bandage protector 610. The final fastener 614 preferably extends to the first end 611A.

The second end region 613B is tapered so as to provide a gradual diminution in the width of the body portion 611 as the second end region extends in a length direction toward the second end 611B. On the wound facing side of the second end region 613B is a frictional portion 616 that provides resistance to motion between the wound/bandage protector 610 and a surface to which it is applied, such as skin, hair, or fur. The frictional portion 616 may have one or more threads made of a rubberized material that provides a moderate amount of friction interwoven in the frictional portion 616 in such a manner that the rubberized material threads are exposed. Alternatively, the frictional portion 616 may be made of a material or a coating that provides a frictional surface. Preferably, the amount of friction provided by the frictional surface of the frictional portion 616 should be one that does not cause discomfort when the wound/bandage protector 610 is worn. The frictional portion 616 may, alternatively, be positioned between the gauze port 612 and the first end region 613A, similar to the strip 62 in the exemplary wound/bandage protector 6 as well as other exemplary embodiments of wound/bandage protectors provided herein. Alternatively, the frictional portion 616 may be provided on another portion of the wound-facing side of the wound/bandage protector 610 that does not conflict with the gauze pad 619, the gauze port 612, or the final fastener 614. Similarly, the other exemplary embodiments of wound/bandage protectors provided herein may have a frictional portion positioned in a similar or equivalent manner as that of wound/bandage protector 610. In addition, the frictional portion 616 of wound/bandage protector 610 may be provided along the top non-wound facing side of the wound/bandage protector 610 and/or the bottom wound facing side of the wound/bandage protector 610.

Figure 16A:
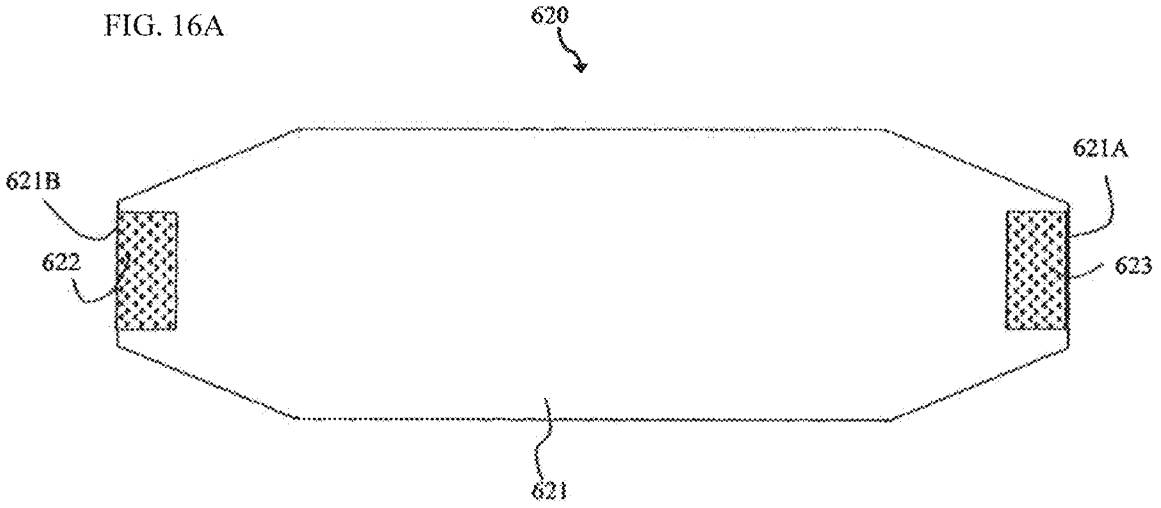
FIG. 16A is a top non-wound facing side view of an exemplary embodiment of a bandage wrap protector/holder according to the present invention.
Figure 16B:
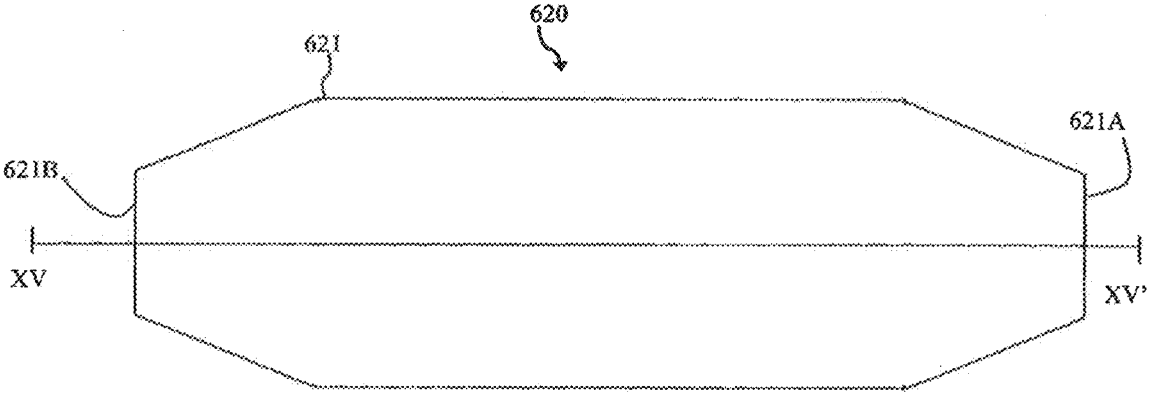
FIG. 16B is a bottom wound facing side view of the exemplary embodiment of the bandage wrap protector/holder illustrated in FIG. 16A.
Figure 16C:
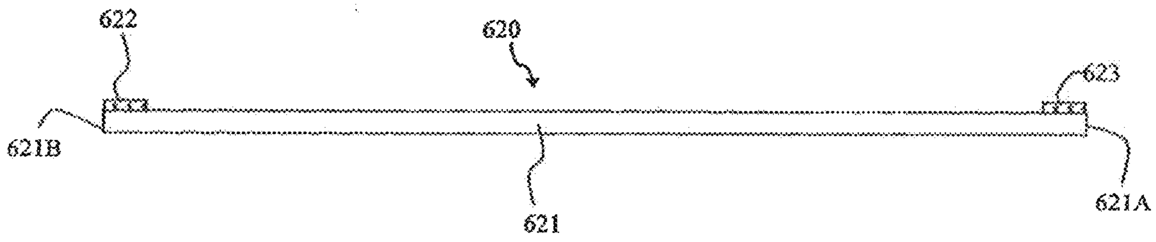
FIG. 16C is a side cross-sectional view of the exemplary embodiment of the bandage wrap protector/holder illustrated in FIGS. 16A and 16B taken along the line XV-XV' in FIG. 16B.

On the second end region 613B is a first-catch fastener 613 on the non-wound-facing side of the wound/bandage protector 610. The first-catch fastener 613 preferably extends to the second end 611B. The first-catch fastener 613 may be made of a Velcro® hook type material so that the first-catch fastener 613 may securely fasten to a portion of the wound facing side of the body portion 611 when the wound/bandage protector 610 is being secured. Thus the first-catch fastener 613, as in all the exemplary wound/bandage protector embodiments disclosed herein, allows for initially securing the wound/bandage protector 610 around a limb by fastening at a first location and then for further tightening and/or securing of the wound/bandage protector 610 by fastening the final fastener 614 to a portion of the non-wound facing side of the wound/bandage protector 610 at a second location. FIGS. 16A to 16C are, respectively, a top non-wound-facing view, a bottom wound facing view, and a cross-sectional side view taken along the line XV-XV' of an exemplary bandage wrap protector/holder 620 according to the present invention. The exemplary embodiment of the bandage wrap protector/holder 620 has a body portion 621 that is preferably comprised of super-stretch material similar to the super-stretch material used in the body 21, 31 of the bandage mittens/socks 20, 30. If the bandage wrap protector/holder 620 is primarily intended to be used as a bandage holder, then the super-stretch material of the body portion 621 may have a relatively high elastic modulus. If the bandage wrap protector/holder 620 is primarily intended to be used as a bandage protector, then the super-stretch material of the body portion 621 may have a relatively low elastic modulus. In the exemplary embodiment, the body portion 621 is configured to act as a loop portion of a Velcro® type fastener on both the bottom wound-facing side of the bandage wrap protector/holder 620 and the top non-wound facing side of the bandage wrap protector/holder 620. Alternatively, the bandage wrap protector/holder 620 may be configured to act as a loop portion of a Velcro® type fastener only on the top non-wound facing side of the bandage wrap protector/holder 620 or the bandage wrap protector/holder 620 may not be configured to act as a loop portion of a Velcro® type fastener at all. The body portion 621 has a length that runs from a first end 621A to a second end 621B with a first end region 623A that extends along the length of the body portion 621 from the first end 621A to a central region 625, the central region 625 extending along the length of the body portion from the first end region 623A to a second end region 623B, and the second end region extending along the length of the body portion from the central region 625 to the second end 621B. The stretchable material of the body portion 621 at least provides such stretching capacity in a manner that allows the length of the body portion 621 to vary. The stretchable material of the body portion 621 may, alternatively, provide such stretching capacity that allows both the length of the body portion 621 as well as a width of the body portion 621 which is perpendicular to the length of the body portion 621 to vary. Both the first end region 623A and the second end region 623B are preferably tapered so as to provide a gradual diminution in the width of the body portion 621 as the first and second end regions 623A, 623B extend lengthwise from the central region 625. On the wound facing side of the bandage wrap protector/holder 620 both the first and second end regions 623A, 623B have fastening portions 624A, 624B that are configured as hook portions of a Velcro® type fastener. The fastening portions 624A, 624B preferably extend to the first and second ends 621A, 621B, respectively.

The exemplary bandage wrap protector/holder 620 may be used in several ways. First, the bandage wrap protector/holder 620 may be used as bandage holder. For example, a limb with a wound that is wrapped with a bandaging material wrap (similar to a regular Ace-type bandage) that can act as a loop portion of a Velcro® type fastener on a non-wound/limb facing side of the bandaging material wrap may be kept closed by the bandage wrap protector/holder 620. (For all exemplary embodiments described herein, other types of fasteners may be implemented and, therefore, for whatever type of fastener is implemented for the bandage wrap protector/holder 620, a complementary fastener would be implemented on the bandaging material wrap.) In such a case, the bandage wrap protector/holder 620 may be secured by one of the fastening portions 624A, 624B to a non-wound/limb facing side of the bandaging material wrap on or close to the external/exposed end of the bandaging material wrap. The wrap protector/holder 620 then is extended rotationally around the bandaging material wrap in the same direction as the bandaging material wrap was wound around the limb and then the other one of the fastening portions 624A, 624B may then be secured to another external/exposed portion of the bandaging material wrap. Alternatively, the wrap protector/holder 620 may be extended entirely around the circumference of the limb and then the other one of the fastening portions 624A, 624B may then be secured to a non-wound facing side of the body portion 621 of the wrap protector/holder 620. In this case, the body portion 621 preferably has a width that is greater than the width of the bandaging material wrap so as to completely cover and protect the bandaging material wrap. It is also preferable in this case that the body portion 621 of the wrap protector/holder 620 be comprised of material that is breathable and water resistant.

Alternatively, the wrap protector/holder 620 may be used as a first catch fastener/holder for the bandaging material wrap by securing one of the fastening portions 624A, 624B to the wound/limb facing side of the bandaging material wrap on or close to the internal/covered end of the bandaging material wrap. The bandaging material wrap may then be wrapped around the circumference of the limb by first extending length-wise away from the body portion 621 and attaching to the wrap protector/holder 620 via the other one of the fastening portions 624A, 624B. Furthermore, the wrap protector/holder 620 may be used in conjunction with one or more fastening bases to cover a wound/bandage.

Figure 17A:
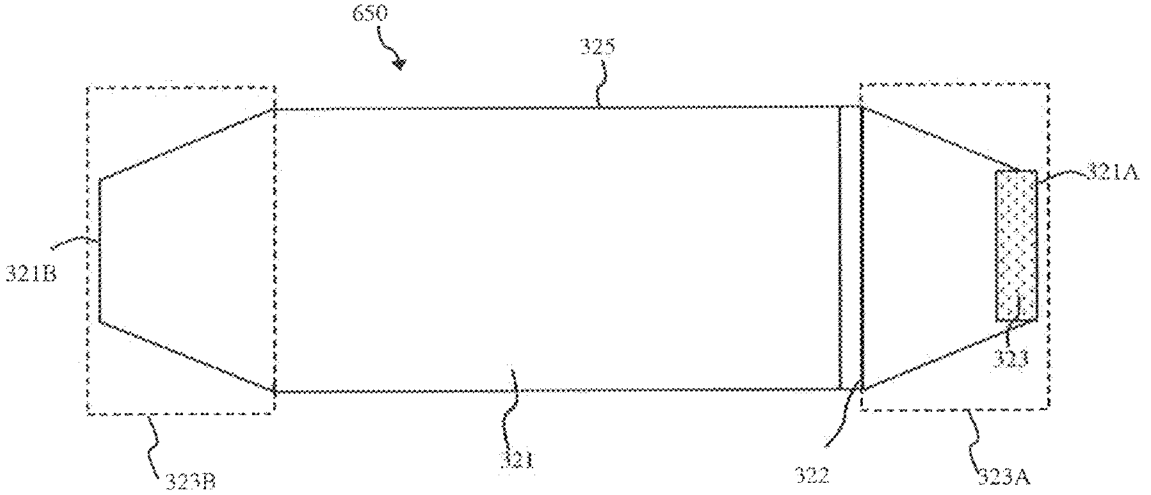
FIG. 17A is a top non-wound facing side view of an exemplary embodiment of an alternative arrangement according to the present invention for the wound/bandage protector illustrated in FIGS. 15A to 15C.
Figure 17B:
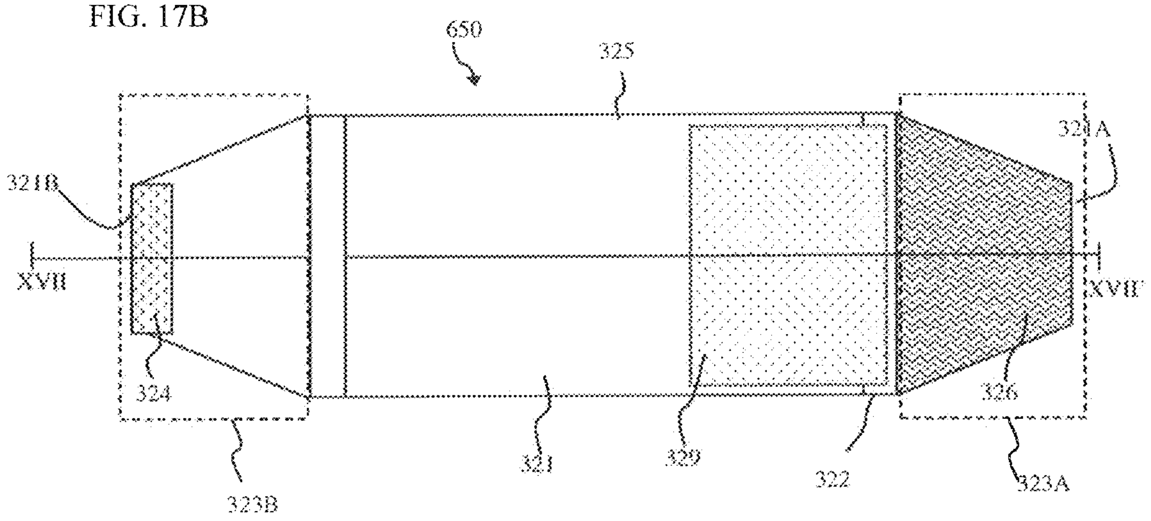
FIG. 17B is a bottom wound facing side view of an exemplary embodiment of the alternative arrangement according to the present invention for the wound/bandage protector illustrated in FIGS. 15A to 15C.
Figure 17C:
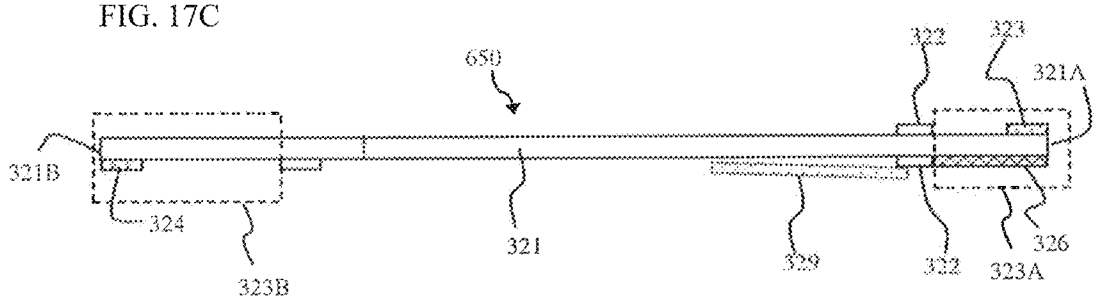
FIG. 17C is a side cross-sectional view of the exemplary embodiment of the wound/bandage protector illustrated in FIGS. 17A and 17B taken along the line XVII-XVII' in FIG. 17B.

FIGS. 17A to 17C illustrate a top non-wound-facing view, a bottom wound facing view, and a cross-sectional side view taken along the line XVII-XVII' of a wound/bandage protector 650, which is an alternative arrangement for the wound/bandage protector 610. In this alternative arrangement, all the elements and structural limitations are the same, except that the frictional portion 326 is positioned on the bottom wound facing side of the wound/bandage protector 650 between the gauze port 322 and the first end 321A, i.e. preferably within the first end region 323A and the first-catch fastener 323 on the non-wound-facing side of the wound/bandage protector 610 within the first end region 323A, while the final fastener 324 is positioned on the wound-facing side of the wound/bandage protector 610 within the second end region 323B. In addition, a portion of the frictional portion 326 may also provide the necessary functionality of the gauze port 322.

Often IV tubes or wires and other conduits need to be kept in place on a patient. Generally this is done with cumbersome and irritating methods using tape. Others, such as U.S. Pat. No. 4,571,245, Hubbard et al., have devised straps with a built-in belt-like wraparound holder, while U.S. Pat. No. 5,292,312, Delk et al., discloses a belt-like wraparound holder that fastens to a base with hook and loop fastener, with the base adhesively attached to a patient. These holders have many disadvantages, the most critical being that they do not provide sufficient stability that is necessary in many instances. These holders allow tubes and wires to be especially susceptible to lateral movement due to inherent instability in the loop formed by the belt-like wraparound holders. They are also susceptible to axial movement if the belt-like wraparound holder is not sufficiently tightened and due to the fact that the configuration of the attachment of the belt-like wraparound holders to the strap in Hubbard and the base in Delk are not sufficiently anchored.

FIGS. 19A and 19B show a bottom-side and a top-side view, respectively of an exemplary embodiment of a wound/bandage protector accessory holder 670. The following discussion of the accessory holder 670 will be with reference to its use with wound/bandage protector 6. However, it should be readily understood that the accessory holder 670 and other accessory holder configurations may be used with other wound/bandage configurations according to the present invention including the exemplary embodiments disclosed herein. In particular, the wound/bandage embodiments with a body portion configured as a wrap and such embodiments do not necessarily have to include such elements that are not relevant to the wound/bandage protector's functionality as an accessory holder such as a gauze pad or gauze port. The accessory holder 670 is an elongate piece of flexible material with a narrow end 672 and a wide end 673. In the wide end is a slit 674 through which the narrow end 672 may extend through. An entire bottom side surface 671 is hook of a hook and loop fastener that can fasten with the non-wound facing side of the wound/bandage protector 6, while an entire top side surface 675 is a high friction-type tacky surface. As with all other discussion regarding hook and loop fastener, it should be readily understood that the hook and loop portion locations may be reversed and other types of fastening systems may be used.

FIGS. 20A to 20C illustrates an exemplary method of using the accessory holder 670 with the wound/bandage protector 60. FIG. 20A is a side view of the wound/bandage protector 6, illustrating only the relevant elements thereof, as it is first being wrapped around a limb 683 but before the wound/bandage protector 60 is fastened.

In FIG. 20B the first catch fastener 63 is fastened with a wound facing side 681 of the body portion 61. Prior to mounting the accessory holder 670 on the body portion 61, the accessory holder 670 may be wrapped around a tube or wire 691 in the manner illustrated in FIG. 21. With the top side 675 of the accessory holder 670 oriented toward the tube or wire 691, the narrow end 672 is bent up (i.e. towards and over the tube or wire 691) and then around the tube or wire 691. A loop 692 is then formed around the tube or wire 691 by inserting and extending the narrow end 672 through the slit 674, the top side surface 675 facing inward toward the tube or wire 691. The accessory holder 670 may then be mounted to wound/bandage protector 6, by fastening the bottom side surface 671 with the non-wound facing side 682 of the body portion 61.

As illustrated in FIG. 20C, once the accessory holder 670 is in place, the final fastener 67 of the fastening tab 64A is fastened to the non-wound facing side 682 of the body portion 61; the fastening tab 64A and the portion of the body portion 61 from where the first catch fastener 63 is fastened to the fastening tab 64A may be stretched and pulled to tighten the wound/bandage protector 6. The body portion 61 and/or the fastening tab 64A thereby cover the accessory holder 670. The portion of the top side surface 675 not within the loop 692 and an exposed portion of the bottom side surface 671 on top of the loop 692 then hold with the tacky surface to the wound facing side 681 of the body portion 61 or the wound facing side of the fastening tab 64A. In an alternative exemplary method, the accessory holder 670 may be first partially mounted on the wound/bandage protector 60 at any point before the portion 67 of the fastening tab 64A is fastened with the non-wound facing side 682 of the body portion 61 and then looped around the tube or wire 691. In an alternative exemplary configuration of the accessory holder 670, a portion of the top side surface 675 may be configured as hook and loop fastener that can fasten with the wound facing side of the body portion 61 and/or the fastening tab 64A, not including the portion 67 of the fastening tab 64A, which fastens with the non-wound facing side 682 of the body portion 61, such that a portion of the top side surface 675 not within the loop 692 may fasten with the wound facing side 681 of the body portion. It should be noted that accessory holders according to the present invention may alternatively mount to a wound facing side, rather than a non-wound-facing side, of a wound/bandage protector between a first location where the first catch fastener fastens with the wound/bandage protector, and a second location where the final fastener fastens with the wound-bandage protector. Alternatively, the super stretch tube 1, any wound/bandage protector according to the present invention, or other possible substrate, may be used to mount an accessory holder thereupon and the wrap protector/holder 620 may then be fastened to the super stretch tube 1, wound/bandage protector or other substrate over the accessory holder. Moreover, the method disclosed here of mounting a tube or wire may also be implemented without an accessory holder.

FIG. 22A shows an alternative exemplary embodiment of an accessory holder 700 according to the present invention. The accessory holder 700 is configured the same way as discussed above by accessory holder 670, with the element numbers and configuration being the same except as specified. In contrast to accessory holder 670, the accessory holder 700 may be configured such that a bottom middle portion 701 of the bottom side surface 671 is configured as a tacky surface with the other remaining portions still being configured as hook of hook and loop type fastener that can fasten with the non-wound facing side 682 of the body portion 61. Additionally, as shown in FIG. 23 the top side surface 675 may be configured with a top middle portion 702 that is hook of a hook and loop fastener that can fasten with the non-wound facing side 682 of the of the body portion 61.

The accessory holder 700 may be wrapped around a tube or wire 691 in the manner illustrated in FIG. 23. The bottom side 671 of the accessory holder 700 is oriented toward the tube or wire 691, the narrow end 672 is bent down (i.e. towards and under the tube or wire 691) and then around the tube or wire 691. A loop 692 is then formed around the tube or wire 691 by inserting and extending the narrow end 672 through the slit 674, the bottom middle portion 701 facing inward toward the tube or wire 691. Once the portion 67 of the fastening tab 64A is fastened to the non-wound facing side 682 of the body portion 61, the top side surface 675 may then frictionally hold to the wound facing side 681 of the body portion 61. If configured, additionally with the top middle portion 702, then an exposed portion of the top middle portion 702 (not shown in FIGS. 22A and 22B) may fasten with the wound facing side 681 of the body portion 61 and/or the wound facing side of the fastening tab 64A, not including the portion 67 of the fastening tab 64A, which fastens with the non-wound facing side 682 of the body portion 61.

FIGS. 25A to 25D show an alternative exemplary embodiment of an accessory holder 730 according to the present invention. The accessory holder 730 may be configured as a flexible piece of material with adhesive on a first side 732 and hook and loop fastener on a second side 731. The first side 732 may be adhered to a tube or wire 733 and the second side 731 forms an outer surface that partially or fully surrounds the tube or wire and that fastens at least with a non-wound facing side of a wound/bandage protector. The accessory holder 730 may have an optional access aperture 735 that allows a second tube or wire 734 to enter into the accessory holder 730.

Figure 29A:
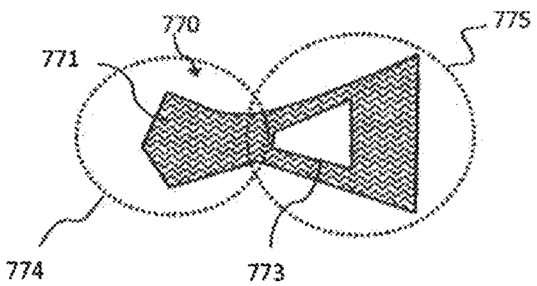
FIG. 29A is a top-side view of an exemplary embodiment of a wound/bandage protector accessory holder.
Figure 29B:
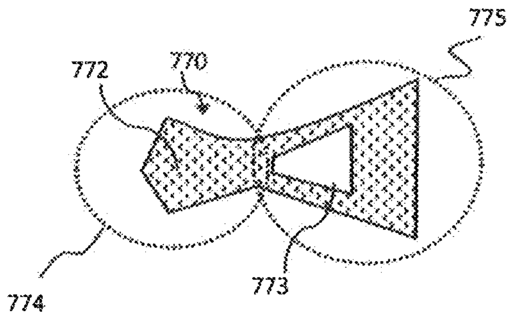
FIG. 29B is a bottom-side view of an exemplary embodiment of a wound/bandage protector accessory holder.

FIGS. 29A and 29B show a top-side and a bottom-side view, respectively of an exemplary embodiment of a wound/bandage protector accessory holder 770. The accessory holder 770 is an elongate piece of flexible material with a narrow end 774 and a wide end 775. In the wide end is an aperture 773 through which the narrow end 774 may extend through. An entire bottom side surface 772 is hook of a hook and loop fastener that can fasten with the non-wound facing side of the wound/bandage protector 6, while an entire top side surface 771 is a high friction-type tacky surface. As with all other discussion regarding hook and loop fastener, it should be readily understood that the hook and loop portion locations may be reversed and other types of fastening systems may be used.

Figure 30A:
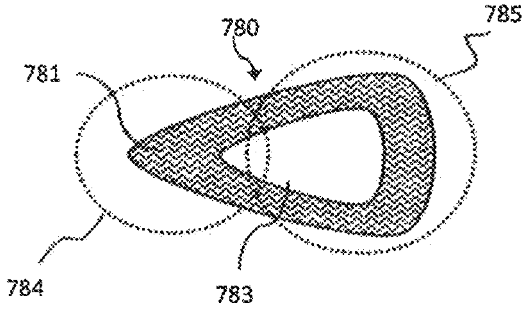
FIG. 30A is a top-side view of an exemplary embodiment of a wound/bandage protector accessory holder.
Figure 30B:
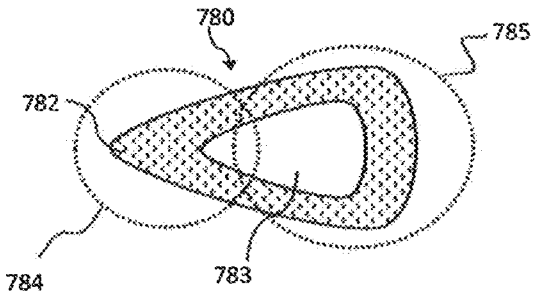
FIG. 30B is a bottom-side view of an exemplary embodiment of a wound/bandage protector accessory holder.

FIGS. 30A and 30B show a top-side and a bottom-side view, respectively of an exemplary embodiment of a wound/bandage protector accessory holder 780. The accessory holder 780 is an elongate piece of flexible material with a narrow end 784 and a wide end 785. In the wide end is an aperture 783 through which the narrow end 784 may extend through. An entire bottom side surface 782 is hook of a hook and loop fastener that can fasten with the non-wound facing side of the wound/bandage protector 6, while an entire top side surface 781 is a high friction-type tacky surface. As with all other discussion regarding hook and loop fastener, it should be readily understood that the hook and loop portion locations may be reversed and other types of fastening systems may be used.

The embodiments of the invention described herein are exemplary in nature, and therefore, the spirit and the scope of the invention are by no means restricted to what is described above or intended to represent every possible embodiment of the invention. For example, when Velcro® is mentioned, the hook portion could be the loop portion and the loop portion could be the hook portion, or it could be a different type of fastening system altogether such as reusable adhesive with a surface that can adhere well to a reusable adhesive or magnetic fasteners, or a self adhering material surfaces, snaps, buttons. Moreover, where reusable adhesive is mentioned, could also be any other form of fastening, or releasable fastening, and in cases where permanent fastening is a possibility, use of other methods of attachment such as heat and punch, radio frequency sealing, ultrasonic sealing or bonding or sewing may also be used. A gauze pad does not need to be square or rectangular it may be any shape that is sufficient to treat a particular wound. The wound/bandage protectors may or may not be configured with a first catch tab and the tab may or may not be configured with a fastener or fastening surface. Likewise, structural limitations discussed by one exemplary embodiment of a wound/bandage protector or sock/mitten or bandage or adhesive bandage may be applied to other exemplary embodiments of the wound/bandage protector or sock/mitten or bandage or adhesive bandage.

What is claimed is:

1. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape;

a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube, wherein at least a portion of the body portion comprises a water resistant material or a waterproof material.

2. The wrapping of claim 1, wherein the stretchable material is a material that stretches to a size that is at least about 10% greater than its unstretched size when subjected to a tension.

3. The wrapping of claim 1, wherein the at least a portion of the non-slip material is disposed on an entirety of the internal side of the body portion.

4. The wrapping of claim 3, wherein the at least a portion of the non-slip material is disposed on an entirety of the external side of the body portion.

5. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape;

a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube; and a dead zone disposed on the body portion.

6. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape, a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube, wherein the non-slip material comprises a silicone material.

7. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape, a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube, wherein the rubberized material is disposed in a continuous manner on the at least a portion of the internal side of the body portion, or is disposed in a discontinuous manner on less than an entirety of the internal side of the body portion.

8. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape, a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube, wherein at least a portion of the tube is breathable.

9. A wrapping, comprising:

a body portion configured as a tube having a first end that is open, a second end that is open, an internal side, and an external side, wherein the tube continuously extends along a circumference of the body portion between the first end that is open and the second end that is open to form a continuous cylindrical shape;

a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the body portion is configured as a tube both when the wrapping is not worn by a wearer and when the wrapping is worn by the wearer, wherein the body portion is always configured as a tube; and a dead zone disposed on the body portion, wherein the dead zone comprises a material that stretches from about 0% to about 9% of its unstretched size when subjected to a tension, wherein the stretchable material is a material that stretches to a size that is at least about 10% greater than its unstretched size when subjected to the tension.

10. The wrapping of claim 9, wherein at least a portion of the body portion comprises a water resistant material or a waterproof material.

11. The wrapping of claim 9, wherein at least a portion of the tube is breathable.

12. The wrapping of claim 9, wherein the rubberized material is disposed in a continuous manner on the at least a portion of the internal side of the body portion, or is disposed in a discontinuous manner on less than an entirety of the internal side of the body portion.

13. The wrapping of claim 9, further comprising:

a fastening strap attached to the external side of the tube, and configured to be wrapped around the tube and fastened with at least a portion of the external side of the tube or an external side of the fastening strap.

14. A wrapping, comprising:

a body portion configured as a tube having a first end that is open, a second end that is open, an internal side, and an external side, wherein at least a portion of the body comprises a water resistant material or a waterproof material, wherein the tube continuously extends along a circumference of the body portion between the first end that is open and the second end that is open to form a continuous cylindrical shape;

a non-slip material disposed on at least a portion of the internal side of the body portion, wherein at least a portion of the non-slip material is formed of a rubberized material, and the rubberized material provides a frictional surface, wherein the non-slip material is adapted to contact a body part upon the body part being inserted through the first end and the second end, wherein at least a part of the body portion is comprised of a stretchable material, wherein the at least a portion of the non-slip material formed of the rubberized material is further disposed on at least a portion of the external side of the body portion, wherein the body portion is configured as a tube both when the wrapping is not worn by a wearer and when the wrapping is worn by the wearer, wherein the body portion is always configured as a tube.

15. The wrapping of claim 14, further comprising:
a dead zone disposed on the body portion,
wherein the dead zone comprises a material that has zero stretch or stretches less than about 10% of its unstretched size when subjected to a tension,
wherein the stretchable material is a material that stretches to a size that is at least about 10% greater than its unstretched size when subjected to the tension.

16. The wrapping of claim 14, further comprising:
a fastening strap attached to the external side of the tube, and configured to be wrapped around the tube and fastened with at least a portion of the external side of the tube or an external side of the fastening strap.

* * * * *